United States Patent
Tsukayama et al.

(10) Patent No.: US 10,363,147 B2
(45) Date of Patent: Jul. 30, 2019

(54) SYSTEM AND METHOD FOR PREPARING A PATIENT'S FEMUR IN AN ORTHOPAEDIC JOINT REPLACEMENT PROCEDURE

(71) Applicant: DePuy Ireland Unlimited Company, County Cork (IE)

(72) Inventors: Craig S. Tsukayama, Fort Wayne, IN (US); Carl F. Livorsi, Lakeville, MA (US); Joseph G. Wyss, Fort Wayne, IN (US); Travis D. Bennett, Huntington, IN (US); Chadd W. Clary, Warsaw, IN (US); Rebecca L. Chaney, Warsaw, IN (US); Daniel E. Lashure, Fort Wayne, IN (US)

(73) Assignee: DePuy Ireland Unlimited Company, Ringaskiddy, County Cork (IE)

(*) Notice: Subject to any disclaimer, the term of this patent is extended or adjusted under 35 U.S.C. 154(b) by 41 days.

(21) Appl. No.: 15/598,503

(22) Filed: May 18, 2017

(65) Prior Publication Data
US 2017/0333209 A1 Nov. 23, 2017

Related U.S. Application Data

(60) Provisional application No. 62/338,276, filed on May 18, 2016.

(51) Int. Cl.
*A61B 17/15* (2006.01)
*A61F 2/46* (2006.01)
(Continued)

(52) U.S. Cl.
CPC ............ *A61F 2/461* (2013.01); *A61B 17/155* (2013.01); *A61B 17/157* (2013.01);
(Continued)

(58) Field of Classification Search
CPC combination set(s) only.
See application file for complete search history.

(56) References Cited

U.S. PATENT DOCUMENTS

| 4,710,075 A | 12/1987 | Davison |
| 4,952,213 A | 8/1990 | Bowman et al. |

(Continued)

FOREIGN PATENT DOCUMENTS

| CN | 101742972 A | 6/2010 |
| CN | 101849864 A | 10/2010 |

(Continued)

OTHER PUBLICATIONS

International Search Report, International Application No. PCT/US2017/033278, dated Aug. 30, 2017, 13 pages.
(Continued)

*Primary Examiner* — David H Willse
*Assistant Examiner* — Javier G Blanco
(74) *Attorney, Agent, or Firm* — Barnes & Thornburg LLP

(57) ABSTRACT

An orthopaedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

2 Claims, 23 Drawing Sheets

(51) Int. Cl.
  *A61F 2/38* (2006.01)
  *A61B 17/16* (2006.01)
  *A61B 17/17* (2006.01)
  *A61F 2/30* (2006.01)
  *A61B 90/00* (2016.01)

(52) U.S. Cl.
  CPC ...... *A61B 17/1631* (2013.01); *A61B 17/1675* (2013.01); *A61B 17/1764* (2013.01); *A61F 2/30734* (2013.01); *A61F 2/385* (2013.01); *A61F 2/389* (2013.01); *A61F 2/3859* (2013.01); *A61F 2/4684* (2013.01); *A61B 2090/033* (2016.02); *A61B 2090/036* (2016.02); *A61F 2002/30604* (2013.01); *A61F 2002/30736* (2013.01); *A61F 2002/3863* (2013.01); *A61F 2002/4687* (2013.01)

(56) References Cited

U.S. PATENT DOCUMENTS

| | | | |
|---|---|---|---|
| 5,100,409 A | 3/1992 | Coates et al. | |
| 5,176,684 A | 1/1993 | Ferrante et al. | |
| 5,356,414 A | 10/1994 | Cohen et al. | |
| 5,415,662 A | 5/1995 | Ferrante et al. | |
| 5,569,259 A | 10/1996 | Ferrante et al. | |
| 5,571,194 A | 11/1996 | Gabriel | |
| 5,601,563 A | 2/1997 | Burke et al. | |
| 5,613,970 A | 3/1997 | Houston et al. | |
| 5,634,927 A | 6/1997 | Houston et al. | |
| 5,681,316 A | 10/1997 | DeOrio et al. | |
| 5,683,397 A * | 11/1997 | Vendrely | A61B 17/155 606/88 |
| 5,702,460 A | 12/1997 | Carls et al. | |
| 5,769,854 A | 6/1998 | Bastian et al. | |
| 5,931,841 A | 8/1999 | Ralph | |
| 5,976,147 A | 11/1999 | LaSalle et al. | |
| 6,488,687 B1 * | 12/2002 | Masini | A61B 17/154 606/88 |
| 6,575,980 B1 * | 6/2003 | Robie | A61B 17/155 606/82 |
| 7,497,874 B1 | 3/2009 | Metzger et al. | |
| 7,744,600 B2 | 6/2010 | Rangaiah et al. | |
| 7,963,968 B2 | 6/2011 | Dees, Jr. | |
| 8,002,777 B2 | 8/2011 | Fox et al. | |
| 8,038,681 B2 | 10/2011 | Koenemann | |
| 8,187,280 B2 | 5/2012 | May et al. | |
| 8,377,141 B2 | 2/2013 | McMinn | |
| 8,425,524 B2 | 4/2013 | Aker et al. | |
| 8,771,280 B2 | 7/2014 | Bailey et al. | |
| 8,986,310 B2 | 3/2015 | Bailey et al. | |
| 9,028,501 B2 | 5/2015 | Thomas et al. | |
| 9,113,915 B2 | 8/2015 | Thomas et al. | |
| 9,579,113 B2 | 2/2017 | Thomas et al. | |
| 9,636,122 B2 | 5/2017 | Chaney et al. | |
| 9,962,173 B2 | 5/2018 | Thomas et al. | |
| 2001/0001121 A1 | 5/2001 | Lombardo et al. | |
| 2003/0114859 A1 | 6/2003 | Grusin et al. | |
| 2004/0039450 A1 | 2/2004 | Griner et al. | |
| 2004/0078043 A1 | 4/2004 | Masini | |
| 2004/0087960 A1 | 5/2004 | Kinnett | |
| 2004/0153087 A1 | 8/2004 | Sanford et al. | |
| 2004/0225368 A1 | 11/2004 | Plumet et al. | |
| 2005/0192588 A1 | 9/2005 | Garcia | |
| 2006/0173463 A1 | 8/2006 | Dees | |
| 2006/0195113 A1 | 8/2006 | Masini | |
| 2006/0241634 A1 | 10/2006 | Tuttle et al. | |
| 2007/0010890 A1 | 1/2007 | Collazo | |
| 2007/0073305 A1 | 3/2007 | Lionberger et al. | |
| 2007/0173850 A1 | 7/2007 | Rangaiah et al. | |
| 2008/0091273 A1 | 4/2008 | Hazebrouck | |
| 2008/0183177 A1 | 7/2008 | Fox et al. | |
| 2008/0228189 A1 | 9/2008 | Fox et al. | |
| 2008/0312659 A1 | 12/2008 | Metzger et al. | |
| 2009/0088762 A1 * | 4/2009 | Koenemann | A61B 17/155 606/88 |
| 2009/0088763 A1 | 4/2009 | Aram et al. | |
| 2009/0125114 A1 | 5/2009 | May et al. | |
| 2009/0204115 A1 | 8/2009 | Dees, Jr. et al. | |
| 2009/0222008 A1 | 9/2009 | Hogg et al. | |
| 2010/0076441 A1 | 3/2010 | May et al. | |
| 2010/0121334 A1 | 5/2010 | Couture et al. | |
| 2010/0234850 A1 | 9/2010 | Dees, Jr. et al. | |
| 2011/0093081 A1 | 4/2011 | Chana et al. | |
| 2011/0218541 A1 * | 9/2011 | Bailey | A61B 17/56 606/88 |
| 2011/0307067 A1 | 12/2011 | Dees | |
| 2012/0310246 A1 * | 12/2012 | Belcher | A61B 17/155 606/80 |
| 2012/0323334 A1 | 12/2012 | Jones et al. | |
| 2013/0144296 A1 | 6/2013 | Yoko et al. | |
| 2013/0165936 A1 | 6/2013 | Myers | |
| 2013/0325014 A1 * | 12/2013 | Sordelet | A61B 17/155 606/82 |
| 2013/0325016 A1 | 12/2013 | Sordelet et al. | |
| 2013/0325018 A1 | 12/2013 | Thomas et al. | |
| 2013/0325019 A1 | 12/2013 | Thomas et al. | |
| 2013/0325021 A1 | 12/2013 | Sordelet et al. | |
| 2013/0325136 A1 | 12/2013 | Thomas et al. | |
| 2014/0276858 A1 | 9/2014 | Major et al. | |
| 2016/0089161 A1 * | 3/2016 | Ardito | A61B 17/1714 606/96 |

FOREIGN PATENT DOCUMENTS

| | | |
|---|---|---|
| CN | 101879099 A | 11/2010 |
| EP | 947169 A2 | 10/1999 |
| EP | 2145590 A1 | 1/2010 |
| EP | 2777550 A2 | 9/2014 |
| EP | 2777556 A2 | 9/2014 |
| FR | 2748389 A1 | 11/1997 |
| FR | 2752519 A1 | 2/1998 |
| FR | 2943528 A1 | 10/2010 |
| GB | 2323037 A | 9/1998 |
| JP | 11104155 A | 4/1999 |
| JP | 2009006066 A | 1/2009 |
| JP | 2010057527 A | 3/2010 |
| WO | 9625123 A2 | 8/1996 |
| WO | 9730661 A1 | 8/1997 |
| WO | 9852499 A1 | 11/1998 |
| WO | 0013597 A1 | 3/2000 |
| WO | 2007041644 A1 | 4/2007 |
| WO | 2007114841 A1 | 10/2007 |
| WO | 2010019284 A1 | 2/2010 |

OTHER PUBLICATIONS

International Search Report, International Application No. PCT/US2017/033278, dated Nov. 21, 2017, 8 pages.

Zimmer NexGen LCCK, Surgical Technique for use with LCCK 4-in-1 Instrument, 2009, 52 pages.

DePuy Orthopaedics, Inc., Sigma Revision and M.B.T. Revision Tray, Surgical Technique, 2008, 82 pages.

Smith & Nephew, Legion, Revision Knee System, Surgical Technique, 2005, 40 pages.

Biomet, Vanguard SSK, Revision System, Surgical Technique, Feb. 2008, 64 pages.

GMK Revision, Surgical Technique, Ret 99.27.12US rev. 1, 1999, 74 pages.

PFC Sigma RP-F, Specialist 2 Instruments, Surgical Technique, Performance in Flexion, 2007, 32 pages.

P.F.C. Sigma Rotating Platform Knee System with M.B.T Tray, Primary Procedure with a Curved or Posterior Stablised Implant, 2003, 43 pages.

LCS High Performance Instruments, Surgical Technique, 2008, 44 pages.

Sigma High Performance Instruments, Design Rationale, 2007, 12 pages.

Sigma High Performance Instruments, Classic Surgical Technique, 2010, 52 pages.

Attune Knee System Surgical Technique, 2013, 73 pages.

(56) References Cited

OTHER PUBLICATIONS

Redacted Memorandum with Appendix A, dated Jan. 26, 2010, outlining a surgical instrument evaluation that commmenced in 2010, 37 pages.
"Reinstall Wave 1 Evaluation Surgical Technique," used during the surgical instrument evaluation that commenced in 2010, 36 pages.
Tray configuration cards showing the instruments used during the surgical instrument evaluation that commenced in 2010, 8 pages.
Declaration of Gary M. Lindsay dated Dec. 23, 2014, 5 pages.
International Search Report and Written Opinion, International Application No. PCT/US2017/033295, dated Dec. 18, 2017, 8 pages.
International Search Report issued in connection with International Application No. PCT/US2017/033307, dated Sep. 25, 2017, 13 pages.

\* cited by examiner

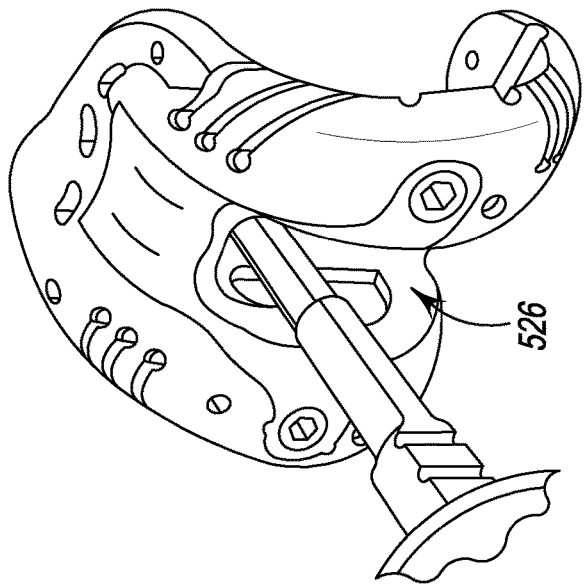
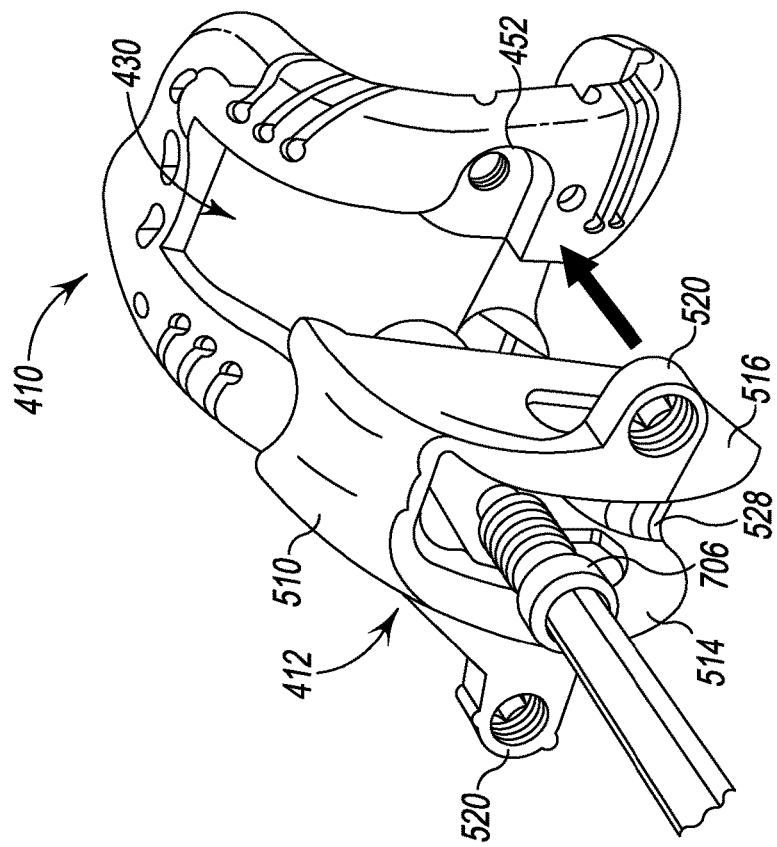
Fig. 13B
Fig. 13A

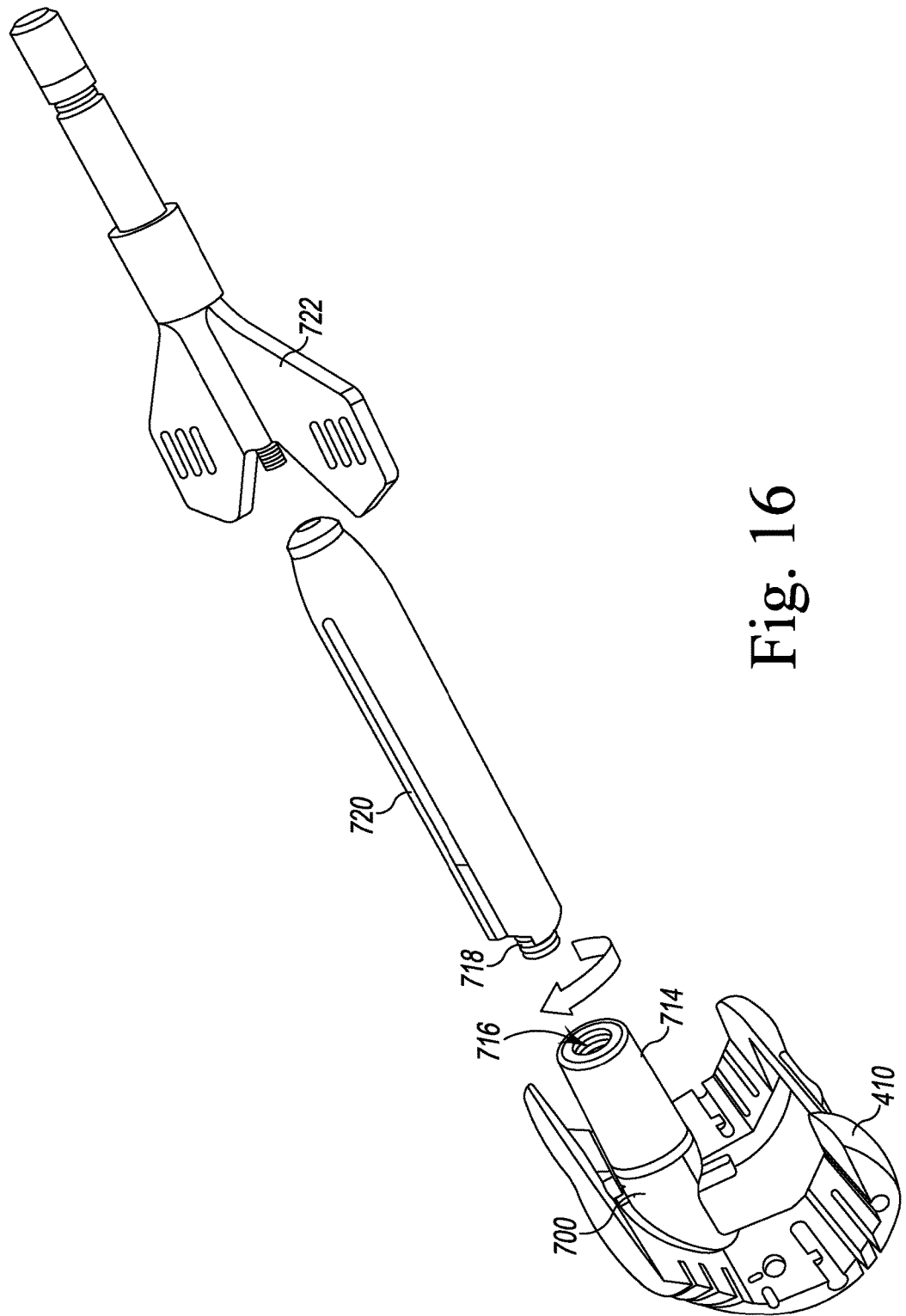

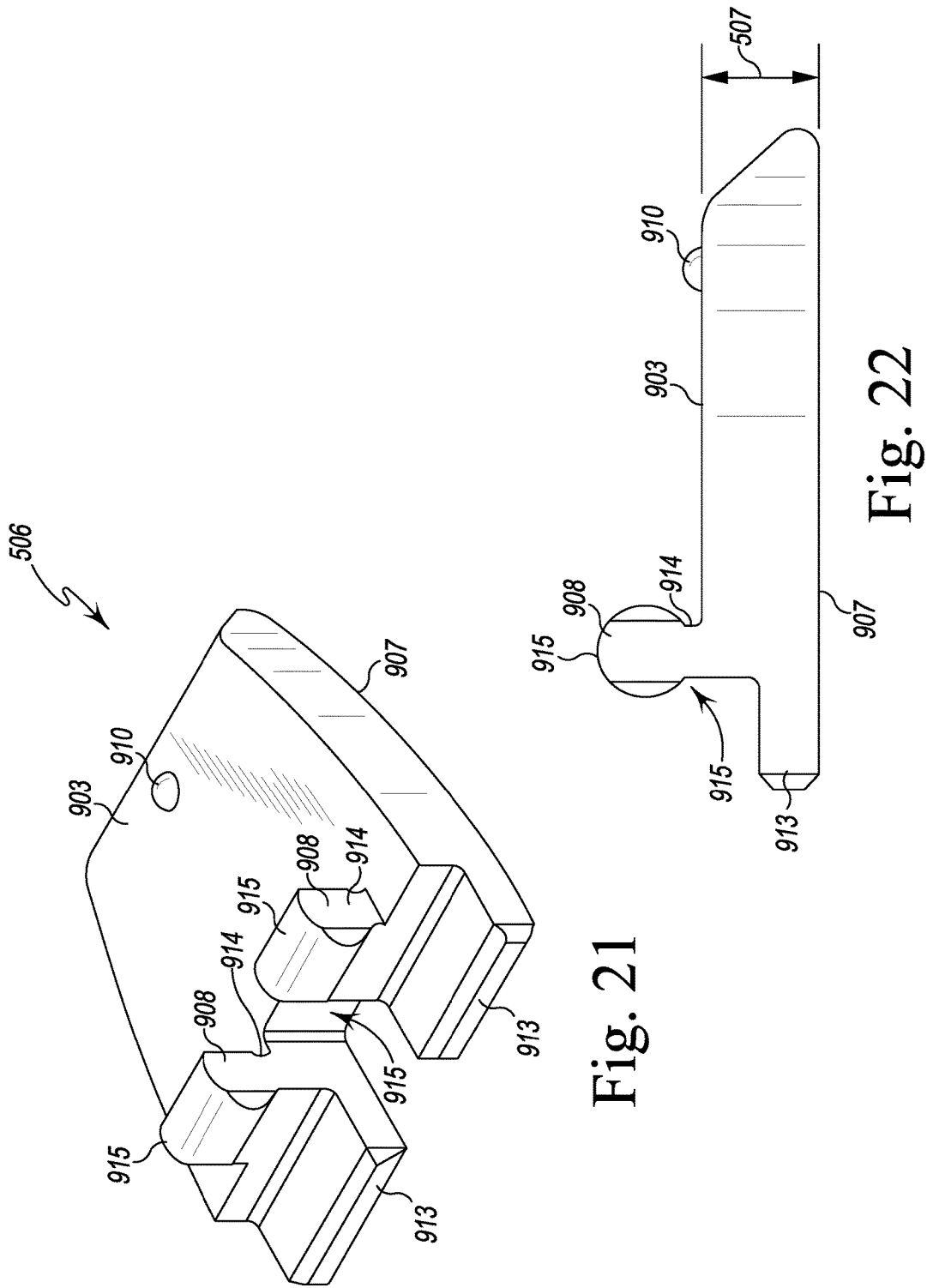

SYSTEM AND METHOD FOR PREPARING A PATIENT'S FEMUR IN AN ORTHOPAEDIC JOINT REPLACEMENT PROCEDURE

The present application claims priority under 35 U.S.C. § 119 to U.S. Patent Application Ser. No. 62/338,276, filed May 18, 2016, and having the title "SYSTEM AND METHOD FOR PREPARING A PATIENT'S FEMUR IN AN ORTHOPAEDIC JOINT REPLACEMENT PROCEDURE," which is herein incorporated by reference in its entirety.

CROSS-REFERENCE TO RELATED APPLICATIONS

Cross reference is made to U.S. Patent Application Ser. No. 62/338,284 entitled "SYSTEM AND METHOD FOR PREPARING A PATIENT'S TIBIA IN AN ORTHOPAEDIC JOINT REPLACEMENT PROCEDURE;" and U.S. Patent Application Ser. No. 62/338,468 entitled "SYSTEM AND METHOD FOR PREPARING A PATIENT'S BONE TO RECEIVE A PROSTHETIC COMPONENT," each of which is assigned to the same assignee as the present application, each of which is filed concurrently herewith, and each of which is hereby incorporated by reference.

Cross reference is made to U.S. patent application Ser. No. 15/598,452 entitled "SYSTEM FOR PREPARING A PATIENT'S FEMUR IN AN ORTHOPAEDIC JOINT REPLACEMENT PROCEDURE"; copending U.S. patent application Ser. No. 15/598,469 entitled "SYSTEM INCLUDING FEMORAL AUGMENT TRIALS AND METHOD OF PERFORMING AN ORTHOPAEDIC JOINT REPLACEMENT PROCEDURE"; copending U.S. patent application Ser. No. 15/598,521 entitled "METHOD FOR PREPARING A PATIENT'S FEMUR IN AN ORTHOPAEDIC JOINT REPLACEMENT PROCEDURE"; and copending U.S. patent application Ser. No. 15/598,533 entitled "SYSTEM AND METHOD OF PERFORMING A REAMING OPERATION ON A PATIENT'S FEMUR DURING AN ORTHOPAEDIC JOINT REPLACEMENT PROCEDURE", each of which is assigned to the same assignee as the present application, each of which was filed concurrently with the present application, and each of which is hereby incorporated by reference.

TECHNICAL FIELD

The present disclosure relates generally to an orthopaedic prosthesis system, including prosthetic components and instruments for use in the performance of an orthopaedic joint replacement procedure, and more particularly to orthopaedic prosthetic components and surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, sometimes referred to as a "primary knee prosthesis," is surgically removed and a replacement or revision knee prosthesis is implanted. In some revision knee surgeries, all of the components of the primary knee prosthesis, including, for example, the tibial tray, the femoral component, and the polymer bearing, may be surgically removed and replaced with revision prosthetic components. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis. Other orthopaedic surgical instruments such as trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a stem trial that may be used to size and select a prosthetic stem component.

SUMMARY

An orthopaedic joint replacement system is shown and described. The system includes a number of prosthetic components configured to be implanted into a patient's knee. The system also includes a number of surgical instruments configured for use in preparing the bones of the patient's knee to receive the implants. A method or technique for using the surgical instruments to prepare the bones is also disclosed.

According to one aspect of the disclosure, an orthopaedic surgical system includes a first surgical reamer including a distal end including a plurality of cutting flutes, a first elongated shaft extending away from the distal end, and a shank configured to be coupled to a surgical drill. The first elongated shaft has a first diameter. A second surgical reamer includes a distal end including a plurality of cutting flutes, a second elongated shaft extending away from the distal end, and a shank configured to be coupled to a surgical drill. The second elongated shaft has a second diameter greater than the first diameter. A depth stop includes a central opening having a third diameter that is equal to the second diameter. The depth stop is configured to be separately coupled to one of the first elongated shaft and the second elongated shaft. The depth stop includes a plurality of alignment tabs extending into the central opening. Each pair of opposing alignment tabs defines a width that is less than the first diameter of the first surgical reamer. A plurality of longitudinal slots are defined in each of the first elongated shaft and the second elongated shaft and each longitudinal slot is sized to receive one of the alignment tabs of the depth stop.

In some embodiments, the first elongated shaft of the first surgical reamer may have a plurality of apertures each positioned at a different distance from the distal end along a longitudinal axis of the first elongated shaft. The depth stop may have a moveable plate operable to separately engage each aperture to secure the depth stop in position along the first elongated shaft. In some embodiments, the second elongated shaft of the second surgical reamer may have a plurality of apertures each positioned at a different distance from the distal end along a longitudinal axis of the second elongated shaft. The moveable plate of the depth stop may be operable to separately engage each aperture to secure the depth stop in position along the second elongated shaft. In some embodiments, the moveable plate may have a pin sized to be received in each aperture. The pin may be configured to extend orthogonal to the longitudinal axes of the first and second elongated shafts. In some embodiments, the pin may extend parallel to a pair of alignment tabs of the depth stop. In some embodiments, each of the first elongated shaft and the second elongated shaft may have a plurality of annular slots. Each annular slot may be associated with one of the apertures and may correspond to a predetermined distance from the distal end.

In some embodiments, the alignment tabs of the depth stop may have a first pair of opposing alignment tabs. A second pair of opposing alignment tabs may extend orthogonal to the first pair of alignment tabs and may cooperate with the first pair of opposing alignment tabs to define an alignment opening in the depth stop. In some embodiments, the depth stop may have a first planar surface and a second planar surface positioned opposite the first planar surface. The central opening may extend through the first planar surface and the second planar surface. The first pair of opposing alignment tabs and the second pair of opposing alignment tabs may extend inwardly from the first planar surface. In some embodiments, the alignment tabs of the depth stop may have a third pair of opposing alignment tabs extending inwardly from the second planar surface. A fourth pair of opposing alignment tabs may extend orthogonal to the third pair of alignment tabs. The fourth pair of opposing alignment tabs may extend inwardly from the second planar surface.

In some embodiments, each longitudinal slot of the first elongated shaft may extend inwardly from an elongated opening defined in the first elongated shaft to a base surface. A first distance may be defined between each opposing base surface of the first elongated shaft. Each longitudinal slot of the second elongated shaft may extend inwardly from an elongated opening defined in the second elongated shaft to a base surface. A second distance may be defined between each opposing base surface of the second elongated shaft. The second distance may be equal to first distance and less than the width of the depth stop. In some embodiments, a guide body may have a passageway sized to receive the first elongated shaft. The depth stop may be configured to engage an outer end of the guide body.

According to another aspect of the disclosure, an orthopaedic surgical system includes a surgical reamer including a distal end including a plurality of cutting flutes, an elongated shaft extending away from the distal end, and a shank configured to be coupled to a surgical drill. The elongated shaft includes a plurality of longitudinal slots and a plurality of apertures defined in a base surface of one of the plurality of longitudinal slots. A depth stop includes a central opening sized to receive the elongated shaft, a moveable plate operable to separately engage each aperture to secure the depth stop in position along the elongated shaft, and a plurality of alignment tabs extending into the central opening and positioned to be received in the plurality of elongated slots of the surgical reamer.

In some embodiments, the moveable plate may have a pin sized to be received in each aperture. The pin may be configured to extend orthogonal to a longitudinal axis of the elongated shaft. In some embodiments, the pin may extend parallel to a pair of alignment tabs of the depth stop. In some embodiments, the elongated shaft may have a plurality of annular slots. Each annular slot may be associated with one of the apertures and may correspond to a predetermined distance from the distal end of the surgical reamer. In some embodiments, the alignment tabs of the depth stop may have a first pair of opposing alignment tabs. A second pair of opposing alignment tabs may extend orthogonal to the first pair of alignment tabs and may cooperate with the first pair of opposing alignment tabs to define an alignment opening in the depth stop. In some embodiments, the depth stop may have a biasing element operable to bias the pin into engagement with the aperture.

According to yet another aspect of the disclosure, a method of performing an orthopaedic surgery includes aligning a central opening of a depth stop with an elongated shaft of a first surgical reamer. The method also includes advancing the depth stop over the elongated shaft to position a plurality of alignment tabs of the depth stop into a plurality of longitudinal slots defined in the elongated shaft. The method also includes securing the depth stop in position along the elongated shaft. The method also includes advancing the first surgical reamer into a guide body to engage the depth stop with the guide body and define an opening in a patient's bone.

In some embodiments, securing the depth stop may require positioning a pin in an aperture defined in the elongated shaft. In some embodiments, the method may require pressing a button to disengage the pin from the aperture.

According to an aspect of the disclosure, an orthopaedic surgical system includes a femoral trial component configured to be coupled to a surgically-prepared distal end of a patient's femur. The femoral trial component includes an anterior flange and a pair of curved arms extending away from the anterior flange. Each arm includes a distal bone-facing surface. A plurality of augment trial components is provided. Each augment trial component is sized to be positioned on the distal bone-facing surface and includes a mounting post and a magnet. Each curved arm includes a slot defined in its distal bone-facing surface that extends inwardly from an outer edge. The slot is sized to receive the mounting post of one of the plurality of augment trial components.

In some embodiments, each augment trial component may have a different thickness. The curved arms of the femoral trial component may have a plurality of distal cutting slots. Each distal cutting slot may be spaced apart from the distal bone-facing surface by a distance equal to the thickness of one of the augment trial components. In some embodiments, each curved arm may have a channel that may be defined in its distal bone-facing surface and extend inwardly from the outer edge parallel to the slot. Each augment trial component may have a peg sized to be received in the channel. In some embodiments, the channel may be partially defined by a tapered surface configured to engage the peg of each augment trial component. In some embodiments, each curved arm may have an aperture that may be defined in its distal bone-facing surface and spaced apart from the channel. Each aperture may be sized to receive the peg of each augment trial component. In some embodiments, each augment trial component may have a planar base surface configured to engage the distal bone-facing surface of each curved arm. The mounting post and the peg may extend outwardly from the base surface.

In some embodiments, a plurality of posterior augment trial components may be provided. Each augment trial component may have a mounting post and a magnet. Each arm may have a posterior bone-facing surface and a posterior slot defined in its posterior bone-facing surface that extends inwardly from the outer edge. The posterior slot may be sized to receive the mounting post of one of the plurality of posterior augment trial components. In some embodiments, each posterior augment trial component may have a different thickness. The curved arms of the femoral trial component may have a plurality of posterior cutting slots. Each posterior cutting slot may be spaced apart from the posterior bone-facing surface by a distance equal to the thickness of one of the posterior augment trial components.

In some embodiments, a femoral trial insert component may be configured to be secured to the femoral trial component. The femoral trial insert component may have a main body sized to be positioned between the pair of curved arms. In some embodiments, a tibial base plate may be sized to be positioned on a proximal surface of a patient's tibia. An insert trial may be configured to be attached to the tibial base plate. The insert trial may have a pair of proximal curved surfaces configured to articulate with the curved arms of the femoral trial component and the femoral trial insert component.

In some embodiments, the mounting post may have a pin operable to retain the mounting post in the slot of the curved arm.

According to another aspect of the disclosure, an orthopaedic surgical system includes a femoral trial component configured to be coupled to a surgically-prepared distal end of a patient's femur. The femoral trial component includes an anterior flange, and a pair of curved arms extending away from the anterior flange. A plurality of augment trial components is provided. Each augment trial component includes a peg and a magnet. Each curved arm includes an aperture defined in a bone-facing surface that is sized to receive the peg of one of the plurality of augment trial components.

In some embodiments, the bone-facing surface may be a distal bone-facing surface. In some embodiments, the bone-facing surface may be a posterior bone-facing surface.

In some embodiments, each curved arm may have a channel that may defined in its bone-facing surface. The channel may extend inwardly from an outer edge of the curved arm and spaced apart from the aperture. The channel may be sized to receive the peg of each augment trial component. In some embodiments, each augment trial component may have a mounting post. Each curved arm may have a slot defined in the bone-facing surface that extends inwardly from the outer edge. The slot may be sized to receive the mounting post of one of the plurality of augment trial components.

In some embodiments, each augment trial component may have a different thickness. The curved arms of the femoral trial component may have a plurality of cutting slots. Each cutting slot may be spaced apart from the bone-facing surface by a distance equal to the thickness of one of the augment trial components.

According to yet another aspect of the disclosure, an orthopaedic surgical system includes a femoral trial component configured to be coupled to a surgically-prepared distal end of a patient's femur. The femoral trial component includes an anterior flange, and a pair of curved arms extending away from the anterior flange. A plurality of augment trial components is provided. Each augment trial component includes a mounting post and a magnet. Each curved arm includes a slot defined in a bone-facing surface that extends inwardly from an outer edge. The slot is sized to receive the mounting post of one of the plurality of augment trial components.

In some embodiments, the bone-facing surface may have a distal bone-facing surface. In some embodiments, the bone-facing surface may have a posterior bone-facing surface.

According to an aspect of the disclosure, an orthopaedic surgical system includes a femoral trial component configured to be coupled to a surgically-prepared distal end of a patient's femur. The femoral trial component includes an anterior flange. A pair of curved arms extends away from the anterior flange. A posterior flange extends between the pair of curved arms. A cutting block is configured to be coupled to the anterior flange of the femoral trial component. The cutting block includes a cutting guide surface. When the cutting block is coupled to the anterior flange of the femoral trial component, the cutting guide surface is positioned coplanar with a distal surface of the anterior flange of the femoral trial component and the posterior flange of the femoral trial component is aligned with the cutting guide surface of the cutting block to prevent further posterior movement of a cutting saw blade.

In some embodiments, the anterior flange of the femoral trial component may have an aperture. The cutting block may have a body having the cutting guide surface and a post extending from the body that may be sized to be received in the aperture.

In some embodiments, the cutting block may have a locking mechanism operable to secure the cutting block to the femoral trial component. In some embodiments, the anterior flange of the femoral trial component may have a slot. The locking mechanism may have a moveable locking tab extending outwardly from the body and sized to be received in the slot. The locking tab may be moveable between a first position in which the locking tab may be configured to engage the anterior flange to secure the cutting block to the femoral trial component and a second position in which the locking tab may be configured to be spaced apart from the anterior flange. In some embodiments, the locking mechanism may have a user-operated button positioned opposite the cutting guide surface. The user-operated button may be operable to actuate the locking tab. In some embodiments, the locking mechanism may have a biasing element to bias the locking tab in the first position.

In some embodiments, the posterior plate may have a groove coplanar with the distal surface of the anterior flange. In some embodiments, the posterior plate may have a visual indicator that may be coplanar with the distal surface of the anterior flange.

In some embodiments, the curved arms of the femoral trial component may have a plurality of distal cutting slots extending parallel to the distal surface of the anterior flange. In some embodiments, the curved arms of the femoral trial component may have a plurality of posterior cutting slots extending orthogonal to the distal cutting slots.

In some embodiments, a tibial base plate may be sized to be positioned on a proximal surface of a patient's tibia. An insert trial may be configured to be attached to the tibial base plate. The insert trial may have a pair of proximal curved surfaces configured to articulate with the curved arms of the femoral trial component.

According to another aspect of the disclosure, an orthopaedic surgical system includes a femoral trial component configured to be coupled to a surgically-prepared distal end of a patient's femur. The femoral trial component includes an anterior flange. A pair of curved arms extends away from the anterior flange. A posterior flange extends between the pair of curved arms. A central passageway is defined between the anterior flange, the curved arms, and the posterior flange. A femoral trial insert component is configured to be secured to the femoral trial component. The femoral trial insert component includes a main body sized to be positioned in the central passageway of the femoral trial component. A cutting block is configured to be coupled to the anterior flange of the femoral trial component. The cutting block includes a cutting guide surface. When the cutting block is coupled to the anterior flange of the femoral trial component, the cutting guide surface is positioned coplanar with a distal surface of the anterior flange of the femoral trial component.

In some embodiments, the main body of the femoral trial insert component may have a curved surface that may be shaped to match a patella surface of a prosthetic femoral component. In some embodiments, the posterior flange of the femoral trial component may be aligned with the cutting guide surface of the cutting block to prevent further posterior movement of a cutting saw blade.

According to another aspect of the disclosure, a method includes coupling a femoral trial component to a surgically-prepared distal end of a patient's femur. The method also includes coupling a cutting block to an anterior flange of the femoral trial component such that a cutting guide of the cutting block is positioned coplanar with a distal surface of the anterior flange. The method also includes advancing a saw blade along the cutting guide of the cutting block and the distal surface of the anterior flange into contact with a patient's femur to cut the patient's femur. The method also includes advancing the saw blade posteriorly to engage the saw blade with a posterior flange of the femoral trial component.

In some embodiments, the method may require cutting the distal end of the patient's femur along an inner surface of each of the medial arm and the lateral arm.

In some embodiments, the method may require positioning a locking tab extending from the cutting block within a corresponding aperture formed in the anterior flange of the femoral trial component to secure the cutting block to the femoral trial component. In some embodiments, the method may require actuating a user-operated button formed on the cutting block to actuate the locking tab. In some embodiments, the method may require coupling a femoral trial insert component to the femoral trial component such that a body of the insert may be positioned in a central passageway defined between a medial arm and a lateral arm of the femoral trial component and between the anterior flange and posterior flange of the femoral trial component. In some embodiments, the method may require articulating the patient's leg between extension and flexion with the femoral trial component engaged with an insert trial component located on a patient's tibia.

According to one aspect of the disclosure, an orthopaedic surgical system includes a tibial base plate sized to be positioned on a proximal surface of a patient's tibia. An insert trial component is configured to be attached to the tibial base plate. The insert trial component includes a pair of proximal curved concave surfaces. A femoral trial component is configured to be coupled to a distal end of a patient's femur. The femoral trial component includes an anterior flange. A pair of curved arms extends away from the anterior flange. Each arm includes a curved condyle surface and a plurality of cutting guide slots. A femoral trial insert component includes a central body sized to be positioned between the pair of curved arms and a pair of mounting flanges extending outwardly from the central body. Each mounting flange includes a distal surface and a fastener retained in each mounting flange to secure the mounting flange to the femoral trial component. The femoral trial component includes a pair of slots in the curved arms sized to receive the mounting flanges of the femoral trial insert component. The distal surfaces and the curved condyle surfaces are configured to engage and articulate on the proximal curved concave surfaces of the insert trial component when the femoral trial insert component is secured to the femoral trial component.

In some embodiments, the femoral trial insert component may have a tab extending outwardly from a first flange of the pair of mounting flanges. The femoral trial component may have a groove defined in a first mounting curved arm of the pair of curved arms. The groove may be connected to a first slot of the pair of slots and may be sized to receive the tab of the femoral trial insert component to orient the femoral trial insert component relative to the femoral trial component. In some embodiments, the pair of curved arms may have a second curved arm devoid of any grooves opening into the other slot of the pair of slots. In some embodiments, the femoral trial insert component may have a second tab extending outwardly from the first mounting flange. The femoral trial component may have a second groove defined in the first curved arm. The second groove may be connected to the first slot and may be sized to receive the second tab of the femoral trial insert component to orient the femoral trial insert component relative to the femoral trial component.

In some embodiments, each fastener may have an elongated threaded shaft sized to engage a threaded bore defined in one of the mounting flanges of the femoral trial component. A head may be connected to the elongated threaded shaft. A socket may be defined in the head. An annular flange may extend radially outward from the head to engage the mounting flange of the femoral trial component. In some embodiments, each mounting flange may have an opening defined in the distal surface of the mounting flange. An inner wall may extend inwardly from the opening to define a cavity in the mounting flange. The inner wall may have a distal section defining a first diameter. The annular flange of the fastener may have a second diameter greater than the first diameter. In some embodiments, the annular flange of the fastener may have a beveled proximal edge.

In some embodiments, the central body of the femoral trial insert component may have an anterior flange. A pair of arms may extend from the anterior flange. Each arm may have one of the mounting flanges. A proximal wall may extend between the pair of arms. The proximal wall may cooperate with the pair of arms and the anterior flange to define a notch sized to receive a spine of the insert trial component. A posterior cam may extend from the proximal wall and may be configured to articulate with the spine of the insert trial component over a range of flexion.

In some embodiments, the femoral trial insert component may be a first femoral trial component. The orthopaedic surgical system may have a second femoral trial component that may have an anterior flange. A pair of arms may extend from the anterior flange. Each arm of the second femoral trial component may have a mounting flange having a distal surface and a fastener retained in the mounting flange to secure the mounting flange to the femoral trial component. An open channel may be defined between the pair of arms.

In some embodiments, the femoral trial insert component may have a post sized to receive a stem trial including an elongated shaft. In some embodiments, the femoral trial insert component may have an anterior surface shaped to match a patella surface of a corresponding femoral prosthetic component.

According to another aspect of the disclosure, an orthopaedic surgical system includes a stem trial including a threaded distal end and an elongated shaft extending from the threaded distal end. A femoral trial component is configured to be coupled to a distal end of a patient's femur. The femoral trial component includes an anterior flange. A pair of curved arms extends away from the anterior flange. Each arm includes a curved condyle surface and a plurality of cutting guide slots. A femoral box trial component includes a central body sized to be positioned between the pair of curved arms. A post is sized to separately receive the threaded distal end of the stem trial. A pair of mounting flanges extends outwardly from the central body. Each mounting flange includes a distal surface and a fastener retained in each mounting flange to secure the femoral box trial component to the femoral trial component. A femoral intramedullary component includes a post sized to separately receive the threaded distal end of the stem trial. Each of a pair of mounting flanges includes a distal surface and a fastener retained in each mounting flange to secure the femoral box trial component to the femoral trial component. The femoral trial component includes a pair of slots in the curved arms sized to separately receive the mounting flanges of the femoral box trial component and the femoral intramedullary component.

In some embodiments, an insert trial component may have a pair of proximal curved concave surfaces configured to articulate with the curved condyle surfaces of the femoral trial component. In some embodiments, the central body may have a posterior cam configured to engage a spine of the insert trial component. In some embodiments, the distal surfaces of the femoral box trial component and the femoral intramedullary component articulate on the proximal curved concave surfaces of the insert trial component when secured to the femoral trial component.

According to another aspect of the disclosure, an orthopaedic surgical system includes a femoral trial component configured to be coupled to a distal end of a patient's femur. The femoral trial component includes an anterior flange. A pair of curved arms extends away from the anterior flange. Each arm includes a curved condyle surface and a plurality of cutting guide slots. A femoral trial insert component includes (i) a pair of mounting flanges extending outwardly from the central body, each mounting flange including a distal surface and a fastener retained therein to secure the mounting flange to the femoral trial component, and a tab extending outwardly from a first flange of the pair of mounting flanges. The femoral trial component includes a pair of slots in the curved arms sized to receive the mounting flanges of the femoral trial insert component and a groove defined in a first mounting curved arm of the pair of curved arms, the groove being connected to a first slot of the pair of slots and sized to receive the tab of the femoral trial insert component to orient the femoral trial insert component relative to the femoral trial component.

In some embodiments, the pair of curved arms may have a second curved arm devoid of any grooves opening into the other slot of the pair of slots. In some embodiments, the femoral trial insert component may have a second tab extending outwardly from the first mounting flange. The femoral trial component may have a second groove defined in the first curved arm. The second groove may be connected to the first slot and sized to receive the second tab of the femoral trial insert component to orient the femoral trial insert component relative to the femoral trial component.

In some embodiments, each fastener may have an elongated threaded shaft sized to engage a threaded bore defined in one of the mounting flanges of the femoral trial component. A head may be connected to the elongated threaded shaft. A socket may be defined in the head. An annular flange may extend radially outward from the head to engage the mounting flange of the femoral trial component. In some embodiments, each mounting flange may have an opening defined in the distal surface of the mounting flange. An inner wall may extend inwardly from the opening to define a cavity in the mounting flange. The inner wall may have a distal section defining a first diameter. The annular flange of the fastener may have a second diameter greater than the first diameter.

According to another aspect, a method of performing an orthopaedic surgical procedure comprises positioning a femoral trial component on a distal end of a patient's femur, advancing a cutting saw blade through a cutting guide slot defined in the femoral trial component to remove a portion of the patient's femur, attaching a femoral trial insert component to the femoral trial component via a pair of fasteners retained on the femoral trial insert component, and engaging surfaces of the femoral trial component and the femoral trial insert component with a pair of concave curved surfaces of a tibial insert trial component over a range of flexion from extension to flexion.

In some embodiments, attaching the femoral trial insert component may include securing the femoral trial insert component to the femoral trial component while the femoral trial component is positioned on the distal end of a patient's femur.

In some embodiments, the method may further comprise attaching an augment trial to a bone-facing surface of the femoral trial component. Additionally, in some embodiments, attaching the augment trial to the bone-facing surface of the femoral trial component may include advancing a mounting post of the augment trial into a slot extending inwardly from an outer edge of the femoral trial component. In some embodiments, attaching the augment trial to the bone-facing surface of the femoral trial component may include engaging a peg of the augment trial with a tapered surface of a channel defined in the bone-facing surface of the femoral trial component to cause the augment trial to tilt relative to the bone-facing surface.

In some embodiments, attaching the femoral trial insert component may include advancing a pair of flanges into openings defined in a pair of curved arms of the femoral trial component. The fasteners may be retained on the pair of flanges. Additionally, in some embodiments, advancing the pair of flanges into openings defined in the pair of curved arms of the femoral trial component includes advancing an alignment tab extending from a first flange of the pair of flanges into an alignment groove defined in a first curved arm of the pair of curved arms. The second curved arm of the pair of curved arms may be devoid of any alignment grooves.

In some embodiments, the method may further comprise attaching a post trial insert component to the femoral trial component via a pair of fasteners retained on the femoral trial insert component, engaging surfaces of the post trial component and the femoral trial insert component with a pair of concave curved surfaces of a tibial insert trial component over a range of flexion from extension to flexion, and removing the post trial insert component from the femoral trial component. The femoral trial insert component may be a femoral box trial component, and attaching the femoral trial insert component to the femoral trial component may include attaching femoral box trial component after removing the post trial insert component from the femoral trial component.

In some embodiments, the method may further comprise coupling a cutting block to an anterior flange of the femoral trial component such that a cutting guide of the cutting block is positioned coplanar with a distal surface of the anterior flange, advancing a saw blade along the cutting guide of the cutting block and the distal surface of the anterior flange into contact with a patient's femur to cut the patient's femur, and advancing the saw blade posteriorly to engage the saw blade with a posterior flange of the femoral trial component. Additionally, in some embodiments, attaching the femoral trial insert component includes attaching the femoral trial insert component to the femoral trial component after advancing the saw blade posteriorly to engage the saw blade with a posterior flange of the femoral trial component.

In some embodiments, the method may further comprise attaching a drill guide body to the femoral trial component via a pair of retained screws, and advancing a surgical reamer through the drill guide body to define an opening in the patient's femur. Additionally, in some embodiments, the method may further comprise securing a depth stop in position along an elongated shaft of the surgical reamer, and advancing the surgical reamer into the drill guide body to engage the depth stop with the guide body.

In some embodiments, may further comprise securing a stem trial to the femoral trial insert component.

According to another aspect, the method of performing an orthopaedic surgical procedure comprises attaching a first femoral trial insert component to a femoral trial component, positioning the first femoral trial insert component and the femoral trial component on a distal end of a patient's femur, and engaging surfaces of the femoral trial component and the first femoral trial insert component with a pair of concave curved surfaces of a tibial insert trial component over a range of flexion from extension to flexion. The method also comprises advancing a cutting saw blade through a cutting guide slot defined in the femoral trial component to remove a portion of the patient's femur, advancing an augment trial medially into a slot defined in the femoral trial component to position a body of the augment trial between a bone-facing surface of the femoral trial component and the patient's femur, and detaching the first femoral trial insert component from the femoral trial component. The method also includes coupling a cutting block to an anterior flange of the femoral trial component, advancing a saw blade along the cutting guide of the cutting block and the distal surface of the anterior flange into contact with a patient's femur to cut the patient's femur, attaching a second femoral trial insert component to the femoral trial component, and engaging surfaces of the femoral trial component and the second femoral trial insert component with a pair of concave curved surfaces of a tibial insert trial component over a range of flexion from extension to flexion.

In some embodiments, the method may further comprise advancing the saw blade posteriorly to engage the saw blade with a posterior flange of the femoral trial component.

In some embodiments, advancing the cutting saw blade through the cutting guide slot may include selecting a cutting guide slot positioned a distance from the bone-facing surface of the femoral trial component that is equal to a thickness of the augment trial component.

In some embodiments, the method may further comprise attaching a drill guide body to the femoral trial component via a pair of retained screws, and advancing a surgical reamer through the drill guide body to define an opening in the patient's femur.

In some embodiments, the method may further comprise securing a stem trial to the first femoral trial insert component prior to attaching the first femoral trial insert component to the femoral trial component.

According to another aspect, the method of performing an orthopaedic surgical procedure comprises positioning a femoral trial component on a distal end of a patient's femur, selecting a cutting guide slot positioned a distance from the bone-facing surface of the femoral trial component that is equal to a thickness of an augment trial component, advancing a cutting saw blade through a cutting guide slot defined in the femoral trial component to remove a portion of the patient's femur, and advancing a mounting post of the augment trial into a slot extending inwardly from an outer edge of the femoral trial component.

In some embodiments, advancing the mounting post of the augment trial into the slot may include positioning a body of the augment trial between a bone-facing surface of the femoral trial component and the patient's femur.

BRIEF DESCRIPTION OF THE DRAWINGS

The detailed description particularly refers to the following figures, in which:

FIGS. 9-11, 12, 12A, 13A, 13B, 14, 15A, 15B, and 16-19 illustrate other steps of the orthopaedic surgical procedure using the orthopaedic joint replacement system.

FIG. 21 is a perspective view of the femoral augment trial shown in FIG. 14;

FIG. 22 is a side elevation view of the femoral augment trial of FIG. 21.

DETAILED DESCRIPTION OF THE DRAWINGS

Figure 1:
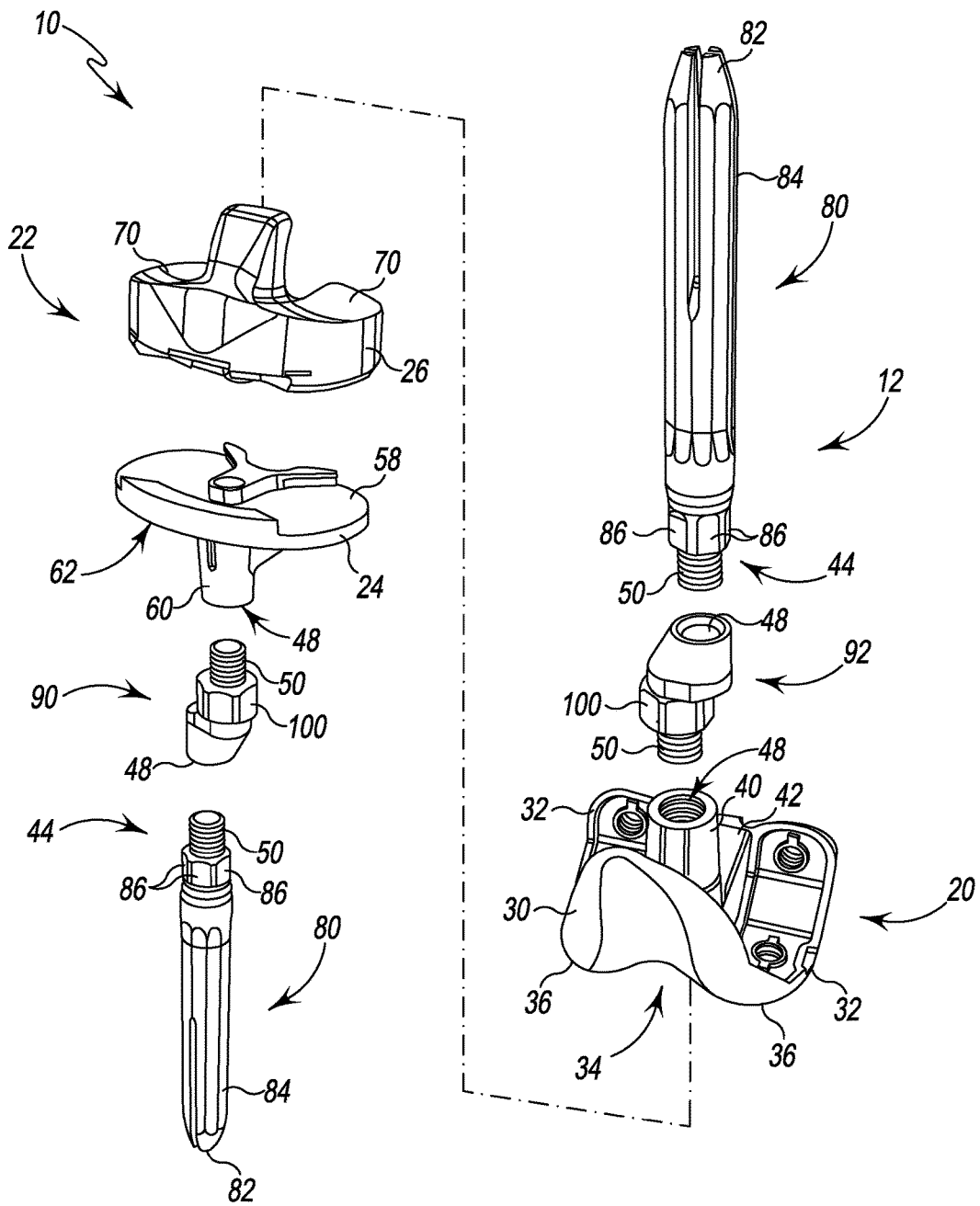
FIG. 1 is an exploded perspective view of prosthetic components of an orthopaedic joint replacement system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referring now to FIG. 1, the orthopaedic joint replacement system 10 includes a number of orthopaedic prosthetic components 12 and a number of orthopaedic surgical instruments 14 (see, for example, FIG. 2) for use in preparing the bone to receive one or more of the prosthetic components 12. What is meant herein by the term "orthopaedic surgical instrument" or "orthopaedic surgical instrument system" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic prosthetic components or implants, such as those shown in FIG. 1.

The prosthetic components 12 of the system 10 include a prosthetic femoral component 20 configured to be secured to a surgically-prepared distal end of a patient's femur and a prosthetic tibial component 22 configured to be secured to a surgically-prepared proximal end of the patient's tibia. In the illustrative embodiment, the tibial component 22 includes a tibial tray 24 and a prosthetic insert 26 configured to engage the femoral component 20 after implantation into a patient's knee. It should be appreciated that the system 10 may include a number of components 12 corresponding to patients having bones of varying sizes. In that way, a surgeon will be able to select the components and other instruments that most-closely match the patient's bony anatomy.

As shown in FIG. 1, the femoral component 20 includes an anterior flange 30 and a pair of condyles 32 extending away from the flange 30. A notch 34, commonly called an intra-condylar notch, is defined between the condyles 32. The condyles 32 define articulation surfaces 36 configured to engage corresponding articulation surfaces 70 of the insert 26. The femoral component 20 also includes an elongated stem post 40, which extends superiorly away from its backside surface 42. As described in greater detail below, the femoral stem post 40 is configured to receive one of a number of different stem components 44. In the illustrative embodiment, a threaded bore 48, which is sized to receive a corresponding threaded shaft 50 of a stem component 44, is defined in the stem post 40.

The tibial tray 24 is configured to be implanted into a surgically-prepared end of a patient's proximal tibia (not shown). The tibial tray 24 includes a platform 58 having an elongated stem post 60 extending inferiorly away from its inferior surface 62. The elongated tibial stem post 60 is configured to receive one of a number of different stem components 44. Specifically, as can be seen in FIG. 1, a threaded bore 48, which is sized to receive a corresponding threaded shaft 50 of a stem component 44, is defined in the stem post 60.

The insert 26 is securable to the tibial tray 24. In particular, the insert 26 may be snap-fit to the tibial tray 24. In such a way, the insert 26 is fixed relative to the tibial tray 24 (i.e., it is not rotatable or moveable in the anterior/posterior or medial/lateral directions). Although, in other embodiments, the tibial tray may be secured in a manner that allows it to rotate relative to the tibial tray 24.

The insert 26 includes lateral and medial articulation surfaces 70. The surfaces 70 are configured to articulate with the corresponding articulation surfaces 36 of the femoral component 20. Specifically, the femoral component 20 is configured to be implanted into a surgically-prepared distal end of the patient's femur (not shown), and is configured to emulate the configuration of the patient's natural femoral condyles. As such, the articulation surfaces 36 of the femoral component 20 are configured (e.g., curved) in a manner which mimics the condyles of the natural femur.

As shown in FIG. 1, the stem components 44 of the system 10 include elongated stems 80, which are configured to be attached to either of the components 20, 22. Each elongated stem 80 extends from the threaded shaft 50 at one end to a pointed tip 82 at the opposite end. Each stem also includes a ribbed outer surface 84 extending from the pointed tip 82 toward the threaded shaft 50. A plurality of substantially planar surfaces 86 are positioned around the outer circumference of the stem 80 adjacent to the shaft 50. The surfaces 86 are sized and positioned to receive the end of a wrench or other installation tool so that the stem 80 may be rotated into tight engagement with one of the threaded bores 48.

In the illustrative embodiment, the prosthetic components 12 also include a plurality of offset adapters 90, 92 configured to be attached to the components 20, 22. As shown in FIG. 1, the adapter 90 is configured to offset the longitudinal axis of the elongated stem 80 from the longitudinal axis of the stem post 60 of the tibial tray 24 by a predetermined amount. Similarly, the adapter 92 is configured to offset the longitudinal axis of the elongated stem 80 from the longitudinal axis of the stem post 40 of the femoral component 20. Each of the adapters 90, 92 includes a threaded shaft 50 configured to be received in the threaded bore 48 of either of the components 20, 22. Each of the adapters 90, 92 also includes a threaded bore 48 at its opposite end, which is sized to receive a threaded shaft 50 of one of the elongated stems 80. In the illustrative embodiment, a locking nut 100 is positioned on the threaded shaft 50 of each of the adapters 90, 92. The locking nut 100 may be tightened against the surface of the stem post of each component to secure the adapter thereto.

The components of the knee prosthesis 10 that engage the natural bone, such as the femoral component 20, the tibial tray 24, and the stem components 44, may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The insert 26 may be constructed with a material that allows for smooth articulation between the insert 26 and the femoral component 20, such as a polymeric material. One such polymeric material is polyethylene such as ultrahigh molecular weight polyethylene (UHMWPE).

Figure 2:
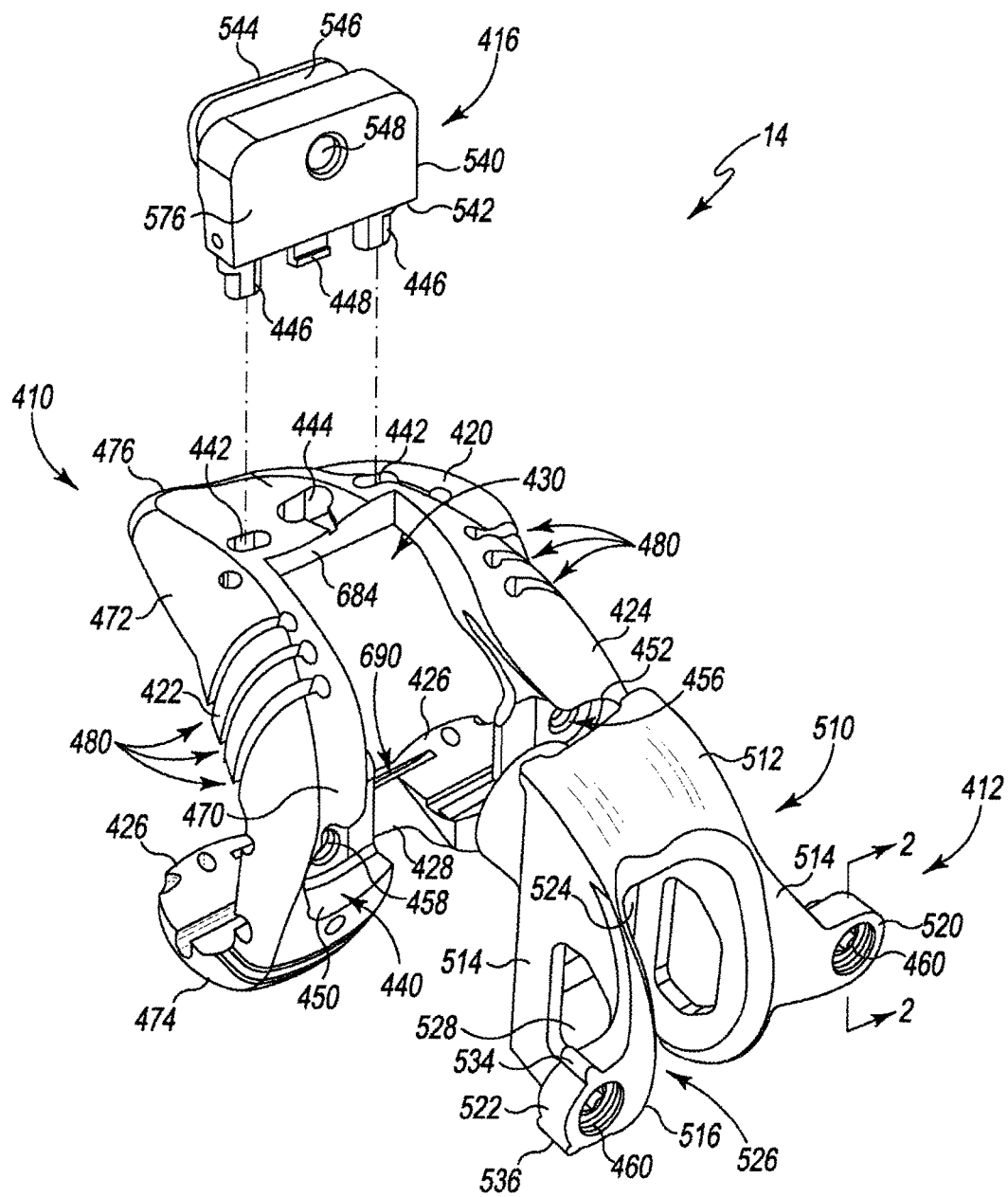
FIG. 2 is an exploded perspective view of surgical instruments of the orthopedic joint replacement system for use in preparing a patient's femur.

Referring now to FIG. 2, a number of orthopedic surgical instruments 14 for use in preparing the femoral bone to receive one or more of the prosthetic components 12 are shown. The instruments 14 include a femoral trial component 410 and a femoral trial insert component 412 configured to be secured to the femoral trial component. The instruments 14 also include a cutting platform or cutting block 416 configured to be coupled to the anterior flange 420 of the femoral trial 410. It should be appreciated that the system 10 may include a number of components 410, 412 and platforms 416 corresponding to patients having femoral bones of varying sizes. In that way, a surgeon will be able to select the components and other instruments that most-closely match the patient's bony anatomy. As described in greater detail below, the surgeon may use the components 410, 412 and the platform 416 to prepare the distal end of a patient's femur to receive the femoral prosthetic components described above in regard to FIG. 1.

The femoral trial component 410 is a monolithic body formed from a metallic material such as, for example, titanium alloy or cobalt chrome alloy, or other suitable biocompatible materials. The component 410 includes an anterior flange 420 and a pair of curved arms 422, 424 extending distally away from the anterior flange 420. Each of the arms 422, 424 extends to a posterior tip 426, and the posterior tips 426 are connected by a posterior plate 428. It should be appreciated that in other embodiments the posterior plate may be omitted. In the illustrative embodiment, the anterior flange 420, arms 422, 424, and posterior plate 428 cooperate to define a central passageway 430 extending through the trial component 410.

As shown in FIGS. 2-5, the trial component 410 includes a plurality of mounting holes and slots 440 that permit the attachment of other surgical instruments, including the femoral trial insert (box trial) component 412 and the platform 416. The mounting holes 440 include a pair of oblong openings 442 defined in the anterior flange 420, and a locking slot 444 positioned between the openings 442. In the illustrative embodiment, the oblong openings 442 are sized to receive a pair of corresponding flanges 446 of the cutting platform 416, while the locking slot 444 is sized to receive a movable locking arm 448 of the cutting platform 416, as described in greater detail below.

Figure 3:
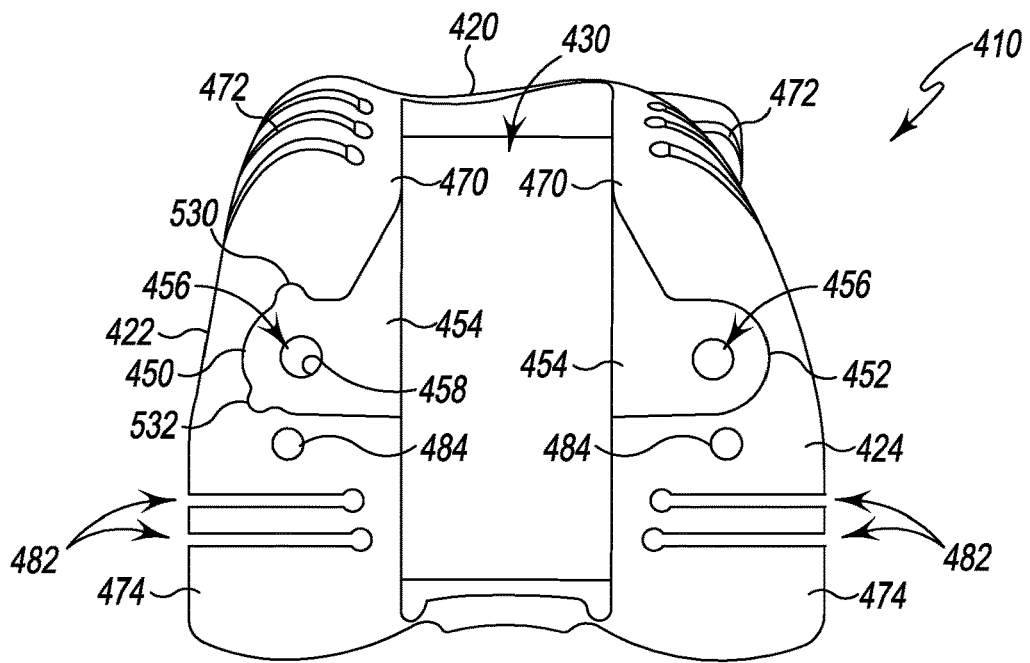
FIG. 3 is a distal plan view of a femoral cutting guide of the surgical instruments of FIG. 2.
Figure 4:
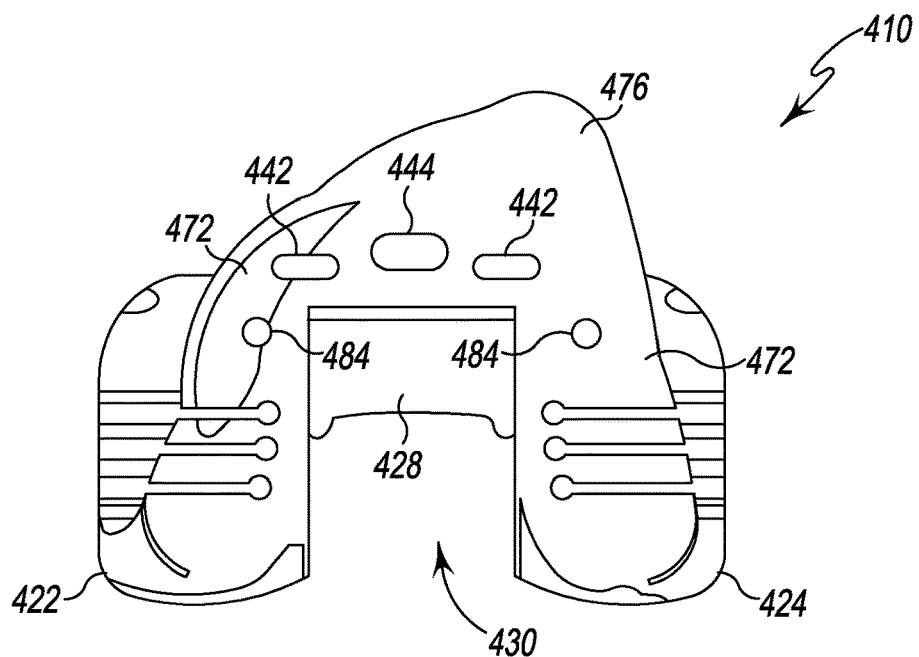
FIG. 4 is an anterior elevation view of the femoral cutting guide of FIGS. 2-3.

The mounting holes 440 also include a pair of apertures 450, 452 defined in the arms 422, 424, respectively, which open into the central passageway 430. As shown in FIGS. 2-3, the base surface 454 of each of the apertures 450, 452 has a through hole 456 defined therein. In the illustrative embodiment, a plurality of threads 458 line the holes 456, and the threads 458 are sized to receive a corresponding pair of fasteners such as, for example, a pair of retained screws 460, of the box trial component 412, as described in greater detail below.

As shown in FIGS. 2-3, the apertures 450, 452 are defined in a distal surface 470 of each of the arms 422, 424. Each of the arms 422, 424 have a curved anterior surface 472 that extends from the distal surface 470 to the anterior flange 420 and a curved posterior surface 474 that extends posteriorly away from the distal surface 470 to the posterior tip 426. The surfaces 470, 472, 474 and the anterior surface 476 of the anterior flange 420 are configured to contact an insert trial component 730 to permit a surgeon to evaluate the range of motion prior to selecting a final set of prosthetic components. In the illustrative embodiment, the contact surfaces of the femoral trial component 410 are shaped to match to the shape of corresponding surfaces of a femoral prosthetic component corresponding to the size of the trial component 410.

The femoral trial component 410 also includes a plurality of cutting slots sized and shaped to guide a surgical saw during the surgical procedure to ensure a predetermined amount of bone is removed with each cut. As shown in FIG. 2, each of the arms 422, 424 includes a plurality of distal cutting slots 480, which are defined in the curved anterior surfaces 472 of the arms 422, 424. Each of the slots 480 corresponds to a different level of distal resection of the femoral bone, with the distal-most slot being used to remove the least amount of bone during the cutting operation and the proximal- or anterior-most slot being used to remove the greatest amount of bone. As shown in FIG. 3, each of the arms 422, 424 also includes a plurality of posterior cutting guide slots 482, which are defined in the curved posterior surfaces 474 of the arms 422, 424. Each of the slots 482 corresponds to a different level of posterior resection of the femoral bone.

Figure 6:
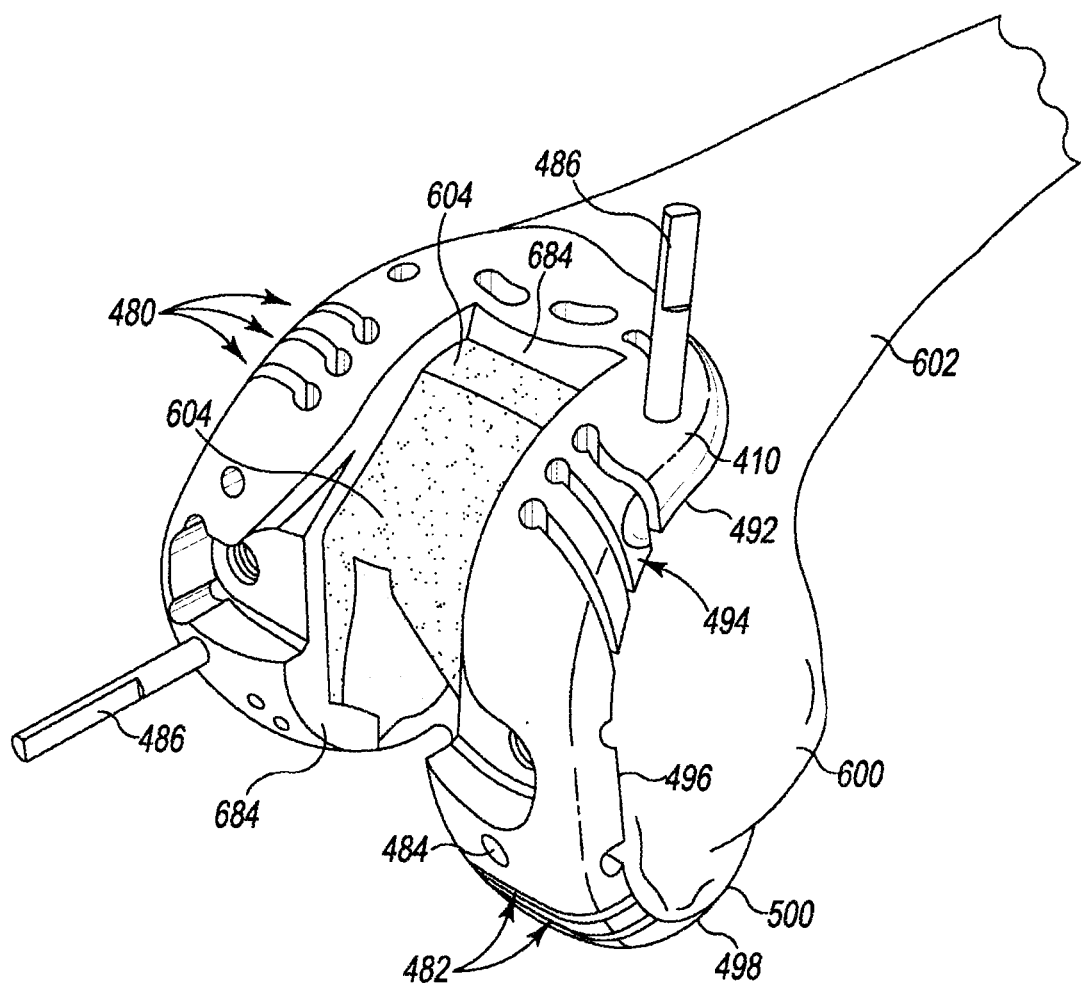
FIGS. 6-7 illustrate steps of an orthopaedic surgical procedure using the orthopaedic joint replacement system.

The trial component 410 also includes a plurality of guide holes 484 sized to permit the passage of fixation pins 486 (see FIG. 6). Such fixation pins may be used to temporarily secure the trial component 410 to the patient's femur during a procedure.

Figure 5:
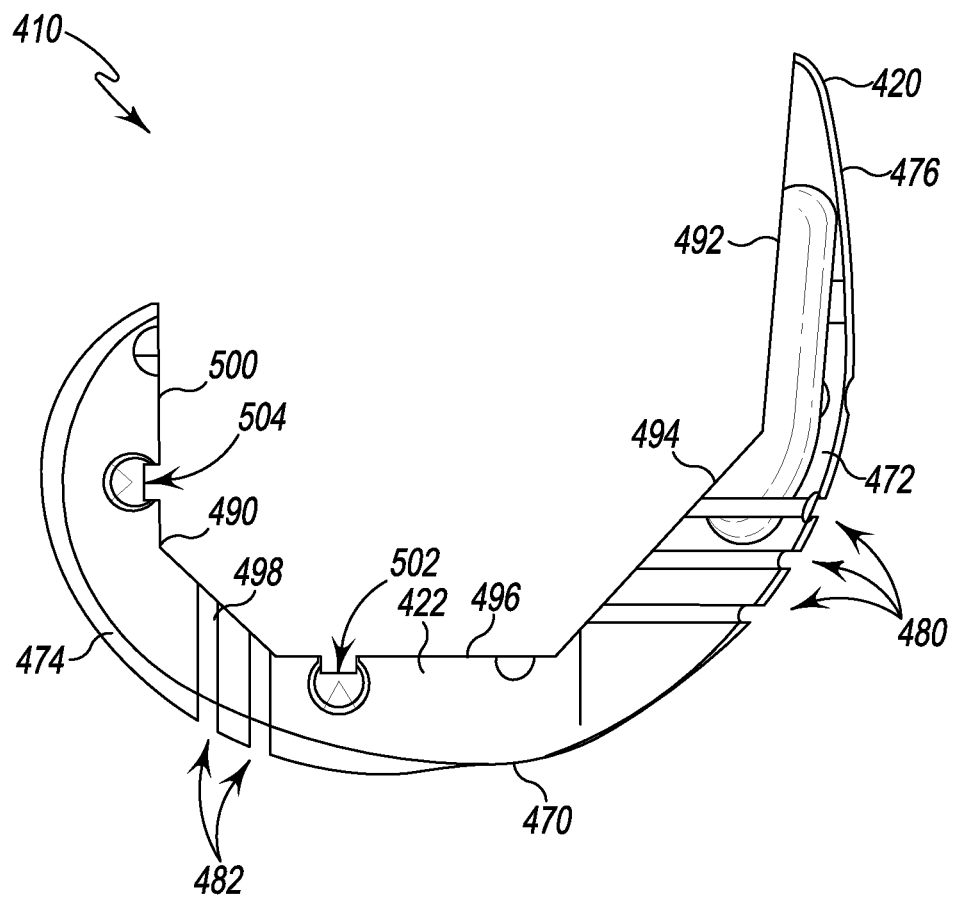
FIG. 5 is a side elevation view of the femoral cutting guide of FIGS. 2-4.

Referring now to FIG. 5, the trial component 410 also includes a bone-facing side 490, which includes surfaces configured to engage the distal end of a patient's femur. The surfaces include an anterior fixation surface 492 positioned opposite the anterior surface 476 of the flange 420. A pair of anterior chamfer surfaces 494 (one for each of the arms 422, 424) extend between the anterior fixation surface 492 and the distal fixation surfaces 496 of the arms 422, 424. Each of the arms 422, 424 also includes a posterior chamfer fixation surface 498 extending between the distal fixation surface 496 and a posterior fixation surface 500. As shown in FIG. 5, the cutting guide slots 480, 482 extend through the fixation surfaces 492, 494, 496, 498, 500 to permit a cutting saw to engage the patient's bone.

In the illustrative embodiment, the surfaces 496, 500 also include mounting slot 502, 504, respectively, which are sized to receive mounting pins or posts 908 of femoral augment trials 506 (see FIGS. 14 and 21-23). It should be appreciated that the system 10 may include a variety of differently-sized femoral augment trials corresponding to different sizes of femoral augment prosthetic components.

Figures 15A, 15B:
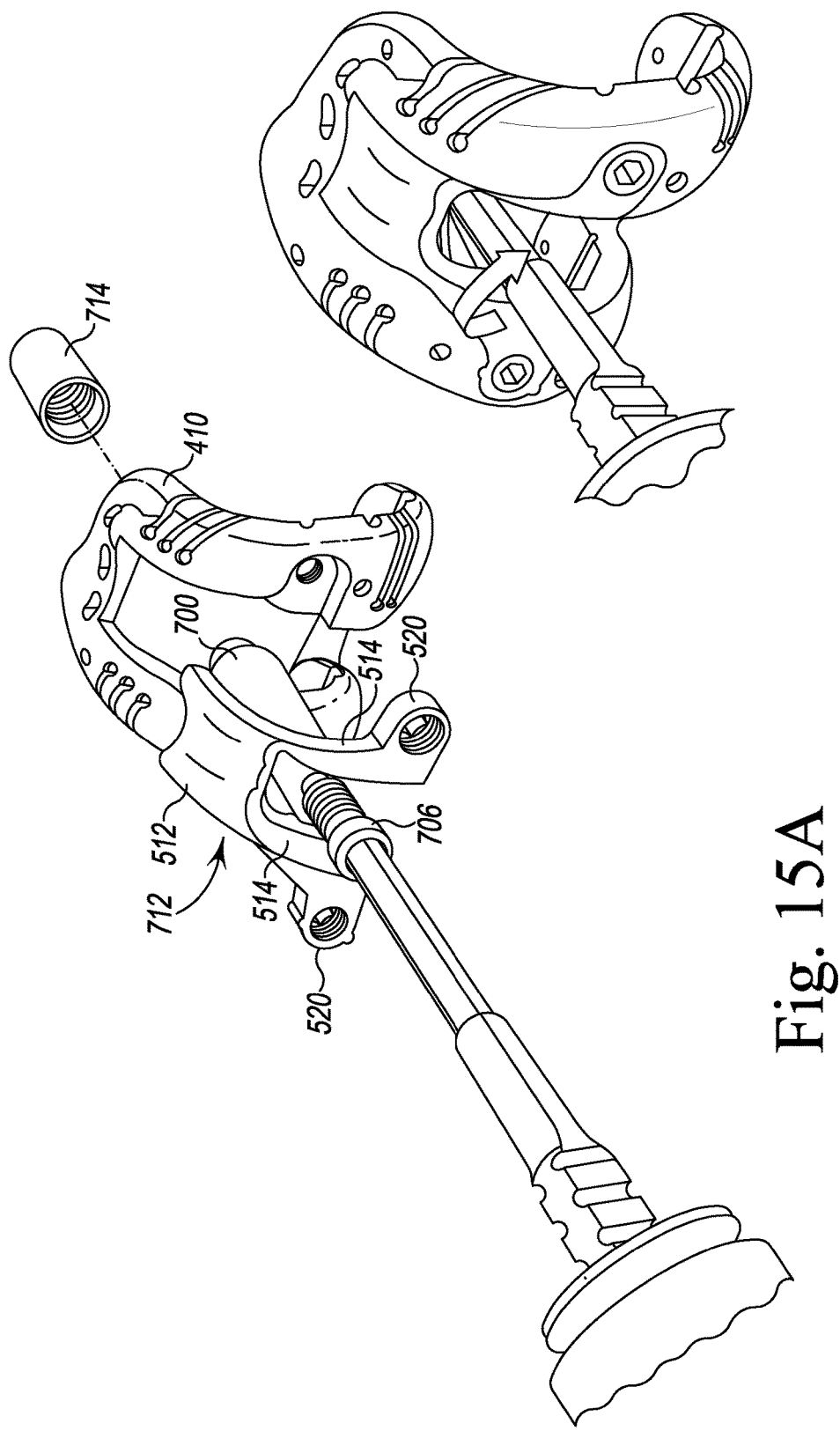

Returning now to FIG. 2, the instruments 14 also include a number of femoral insert trial components, including the box trial component 412 shown in FIG. 2 and the post trial component 712 (see FIGS. 15-16), which are configured to be separately attached to the femoral trial component 410. In the illustrative embodiment, the box trial component 412 includes a central body 510 sized to be positioned in the central passageway 430 of the trial component 410. The body 510 includes an anterior flange 512 having a surface shaped to match the patella surface of a corresponding femoral prosthetic component. The body 510 also includes a pair of arms 514 extending from the flange 512. Each arm 514 also includes a curved surface 516 shaped to match a corresponding surfaces of the femoral prosthetic component. In that way, when the box trial component 412 is secured to the femoral trial component 410, the components 410, 412 may cooperate to permit a surgeon to evaluate the range of motion and select a set of prosthetic components.

The box trial component 412 has a pair of mounting flanges 520, 522 that extend outwardly from the arms 514. The mounting flanges 520 are sized and shaped to be received in the apertures 450, 452 of the femoral trial component 410, as described in greater detail below. A proximal wall 524 extends between the pair of arms 514 and cooperates with the arms 514 and the anterior flange 512 to define a notch 526 in the box trial component 412. The notch 526 is sized to receive a spine 738 (see FIG. 19) of an insert trial component 730. As shown in FIG. 1, the box trial component 412 also includes a posterior cam 528 that is configured to articulate with the spine 738 over a range of flexion.

Figure 2A:
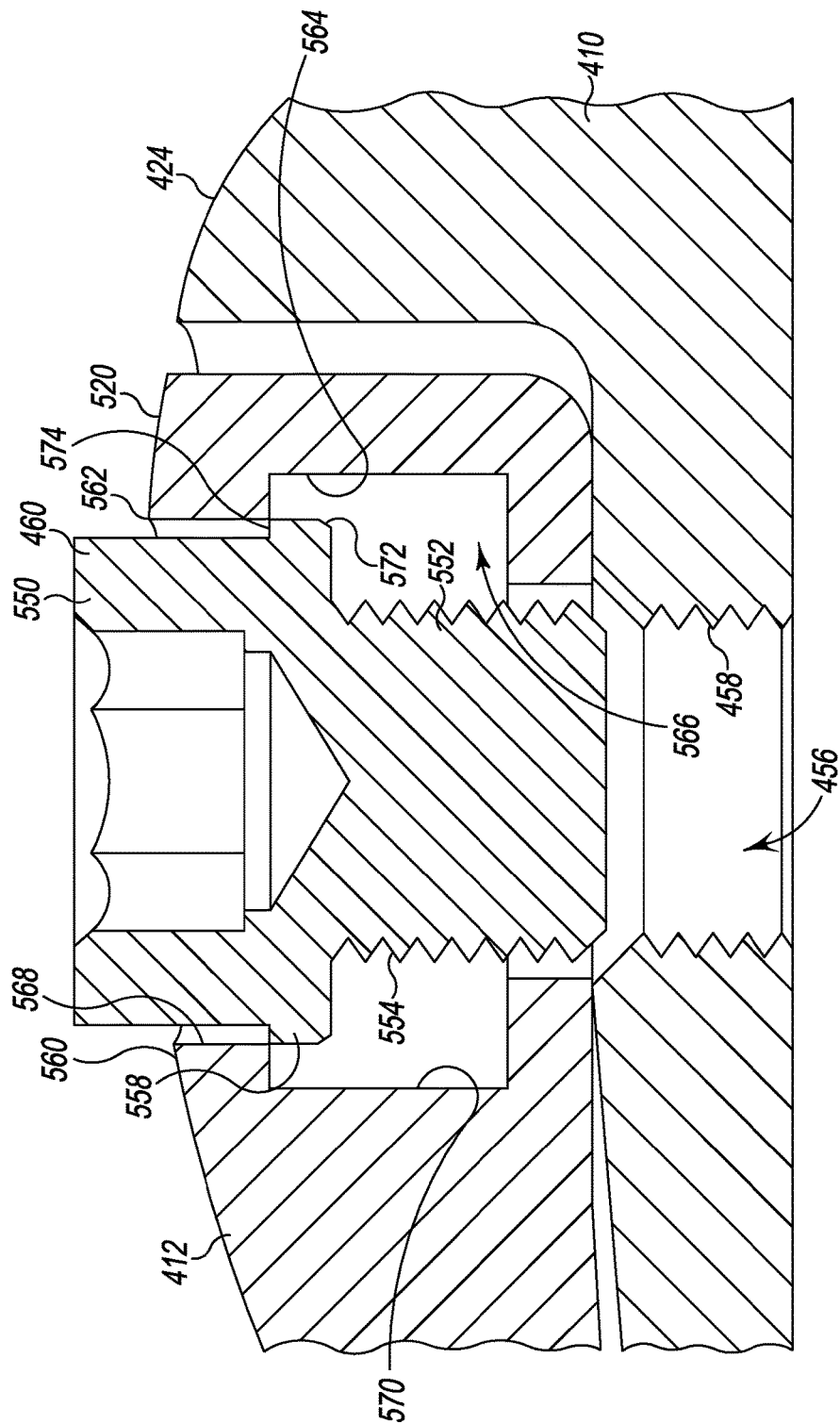
FIG. 2A is a cross-sectional side elevation view taken along the line 2-2 in FIG. 2.

The box trial component 412 also includes a pair of fasteners 460, which are attached to the flanges 520 and are configured to be received in the threaded holes 456 of the trial component 410 to secure the box trial component 412 thereto. As shown in FIG. 2A, each fastener 460 includes a head 550 and an elongated body 552 extends from the head 550. The elongated body 552 includes a plurality of threads 554 configured to engage the threaded surface 458 of the hole 456 defined in the femoral trial component 410. Each fastener 460 also includes an annular plate 558 that extends outwardly from the head 550 to attached the fastener 460 to the flange 520 of the femoral trial insert component 412.

Each flange 520 of the femoral trial insert component 412 includes a distal surface 560 that is shaped to match the posterior surfaces 474 of the femoral trial component 410. Each flange 520 also has an opening 562 defined in the distal surface 560, and an inner wall 564 that extends inwardly from the opening 562 to define a passageway 566 extending through the flange 520. As shown in FIG. 2A, the fastener 460 is retained in the passageway 566. In the illustrative embodiment, the inner wall 564 includes a distal section 568 and a central section 570 that is larger than the distal section 568. The distal section 568 is also smaller in diameter than the diameter of the annular plate 558 of the fastener 460 to retain the fastener 460 into the passageway 566. The plate 558 also includes a chamfered proximal edge 572 such that, during assembly, an assembler may press the chamfered proximal edge 572 into the opening 562 to advance the fastener 460 into the passageway 566. The planar distal edge 574 of the plate 558 prevents removal of the fasteners 460.

In the illustrative embodiment, the femoral trial component 410 and the box trial component 412 include additional features to prevent the component 410, 412 from being improperly assembled. As shown in FIG. 3, a pair of notches 530, 532 are defined in the outer perimeter of the aperture 450 of the femoral trial component 410. A corresponding pair of tabs 534, 536, respectively, extend outwardly from the flange 522 of the box trial component 412 and are sized to be received in the notches 530, 532. As shown in FIG. 3, the other aperture 452 of the femoral trial component 410 lacks any such notches so that a surgeon would be unable to assemble the components 410, 412 with the flange 522 in the aperture 452. It should be appreciated that the notches of the femoral trial component and the flanges of the box trial component may be moved to different positions depending on the component sizes. In that way, these features may be used to ensure that only the box trial component that has the same size as the femoral trial component may be secured to that femoral trial component. It should also be appreciated that other features may be used to prevent improper assembly of the components.

Returning again to FIG. 2, the instruments 14 also include a cutting guide platform 416 having a cutting guide surface 576. The platform 416 includes a body 540 including a posterior surface 542 shaped to engage the anterior surface 476 of the flange 420 such that the cutting guide surface 576 is positioned coplanar with a distal surface 684 of the anterior flange 420 and is aligned with the posterior plate 428 to prevent further posterior movement of a cutting saw blade, when the cutting saw blade is advanced posteriorly along the cutting guide surface 576. In the illustrative embodiment, the posterior plate 428 includes a groove 690 that is coplanar with the distal surface 684 of the anterior flange 420. In some embodiments, the posterior plate 428 includes a visual indicator that is coplanar with the distal surface 684 of the anterior flange 420. As described above, the platform 416 also includes a pair of flanges 446, which extend outwardly from the posterior surface 542. The platform 416 also includes a locking mechanism 544 configured to secure the cutting platform 416 to the trial component 410. In the illustrative embodiment, the locking mechanism 544 includes the locking arm 448 (and its engagement tab) and a user-operated button 546 attached to the body 540. A spring or other biasing element 548 biases the button 546 in the position shown in FIG. 2.

When the posterior surface 542 of the platform 416 is engaged with the anterior surface 476 of component 410, the flanges 446 are received in the slots 442 defined in the component 410, and the engagement tab of the locking arm 448 engages the anterior fixation surface 492 of the flange 420, thereby securing the platform 416 to the component 410. To detach the platform 416 from the component 410, the surgeon may depress the button 546, thereby compressing the spring 548 and rotating the locking arm 448 out of engagement with the fixation surface 492. The surgeon may then withdraw the locking arm 448 and flanges 446 from the component 410 before releasing the button 546.

As described above, the instruments 14 may be used to surgically prepare a patient's femur to receive a prosthetic femoral component 20 and one of the stem components 44. In the illustrative embodiment, the instruments 14 may be used in a revision procedure in which a primary implant has been removed from a distal end of the patient's femur. As shown in FIG. 6, the distal end 600 of a patient's femur 602 in a revision procedure includes a plurality of surfaces 604 that had been previously-shaped to receive the primary implant. During a revision procedure, the surfaces 604 are resected to prepare the distal end 600 to receive the prosthetic femoral component 20. FIGS. 6-19 and 23 illustrate a number of exemplary steps of a procedure for surgically-preparing the distal end 600 during a revision procedure. It should be appreciated that any surgical procedure may include additional or fewer steps depending on the state of the patient's bony anatomy and the preferences of the surgeon.

Referring now to FIG. 6, a surgeon may select an appropriately-sized femoral trial component 410 to be positioned on the distal end 600 of the patient's femur 602. When the surgeon has selected a trial component 410, the surgeon may advance the trial component 410 over the distal end 600 to engage the fixation surfaces 492, 494, 496, 498, 500 of the trial component 410 with the distal end 600. The surgeon may then secure the trial component 410 to the patient's femur 602 via one or more fixation pins 486. To do so, surgeon may align a fixation pin 486 with one of the guide holes 484 and then advance the pin 486 through the guide hole 484 into the patient's femur 602. With the femoral trial component 410 attached to the bone, the surgeon may use it to perform a reaming operation on the patient's femur 602. The surgeon may also perform one or more resections using the cutting guide slots 480, 482 of the trial component 410.

Figure 7:
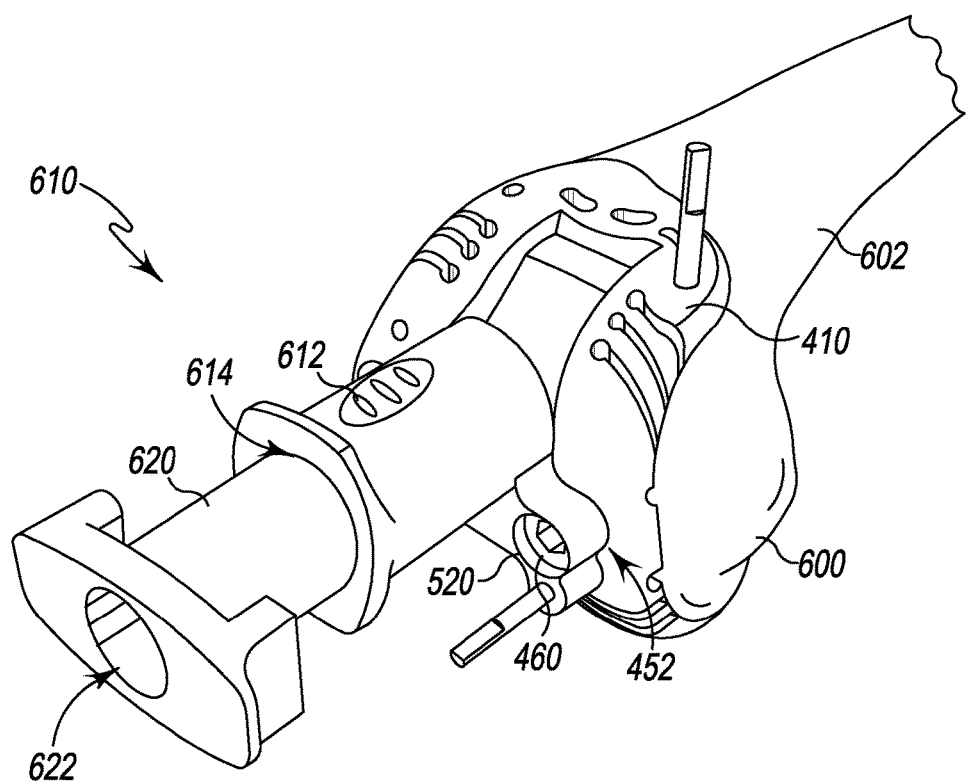

As shown in FIG. 7, a reaming guide 610 may be attached to the trial component 410 via the apertures 450, 452 in a manner similar to that described above in regard to the box trial component 412. The reaming guide 610 includes a barrel-shaped body 612 and a pair of mounting flanges 520 that extend outwardly from one end of the body 612. The mounting flanges 520 are sized and shaped to be positioned within the apertures 450, 452 and include retained fasteners 460 configured to be received in the threaded holes 456 of the trial component 410. A central cylindrical passageway 614 extends through the body 612 to permit the passage of a surgical reamer. In the illustrative embodiment, the reaming guide 610 also includes an adapter 620 sized to be positioned in the central passageway 614. As shown in FIG. 7, the adapter 620 has a central cylindrical passageway 622 of smaller diameter than the passageway 614. In that way, the reaming guide 610 may be used with reamers of varying size.

Figure 8:
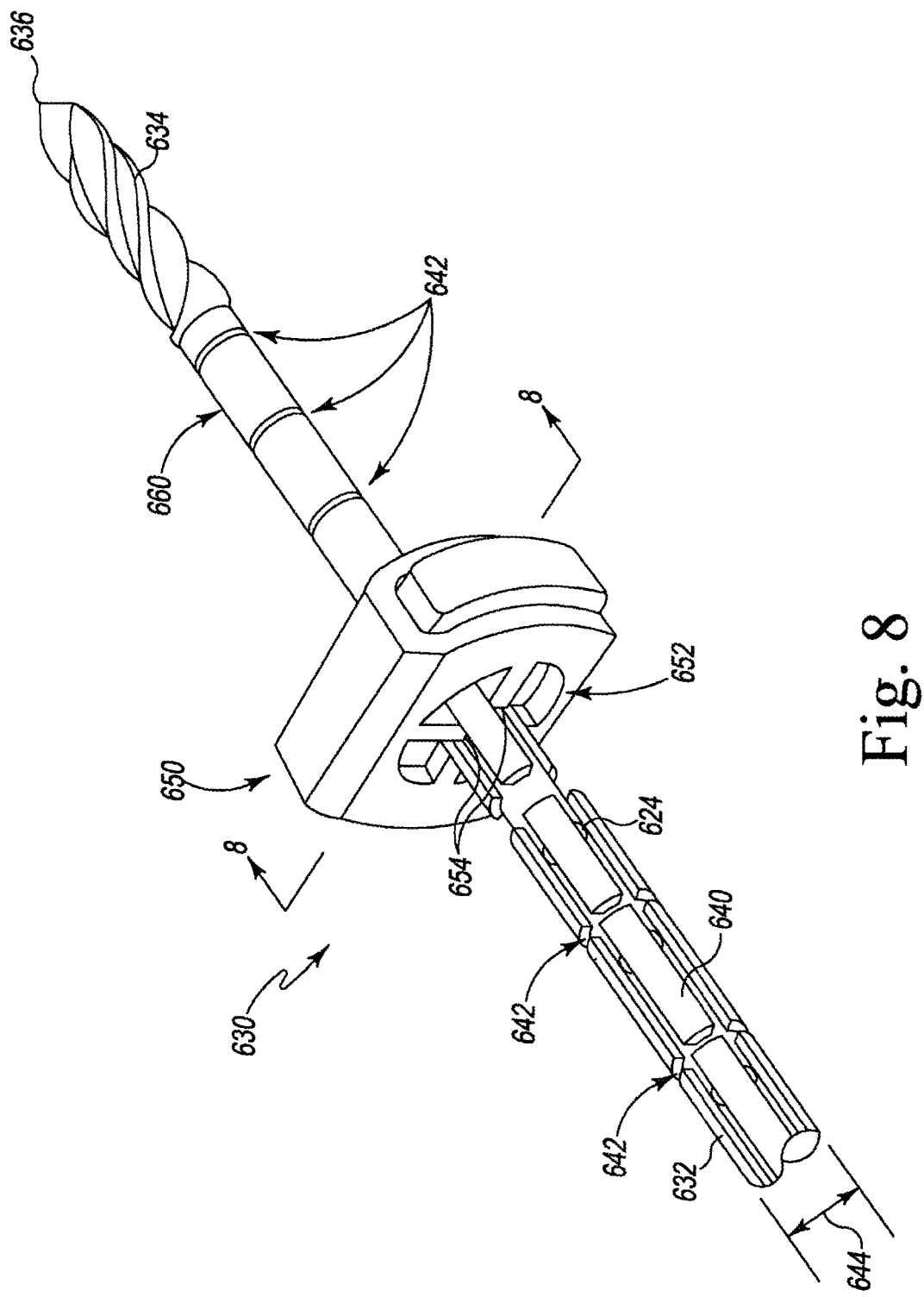
FIG. 8 is a perspective view of a pair of surgical instruments of the orthopedic joint replacement system.

Referring now to FIG. 8, one surgical reamer 630 for use with the reaming guide 610 is shown. The reamer includes an elongated shaft 632 having a plurality of cutting flutes 634 formed at a distal end 636. A tool shank (not shown) is formed at the opposite end and is sized to be secured to a surgical drill or other rotary surgical instrument. The elongated shaft 632 includes a cylindrical outer surface 640 that extends from the cutting flutes 634 to the tool shank. A plurality of spaced-apart annular slots 642 are defined in the outer surface 640. In the illustrative embodiment, the position of each annular slot 642 along the outer surface 640 corresponds to a desired reaming depth of the reamer 630, which, in turn, corresponds to a desired depth for a stem component 44.

The outer surface 640 of the shaft 632 defines a diameter 644 of the reamer 630. In the illustrative embodiment, the instrument 14 includes a plurality of different reamers having a similar configuration to reamer 630 but with larger diameters.

The system 10 also includes a moveable depth stop 650, which may be attached to the reamer 630 at the annular slot 642 corresponding to a desired depth. In the illustrative embodiment, the depth stop 650 has a central opening 652 and a plurality of alignment tabs 654 extending inwardly into the opening 652. The central opening 652 has a diameter corresponding to the diameter of the central passageway 614 of the reaming guide 610, which corresponds to the largest diameter reamer in the system 10. Each reamer, including the reamer 630, includes a plurality of longitudinal slots 660 corresponding in number to the number of alignment tabs 654 of the depth stop 650. Each of the longitudinal slots 660 includes apertures or notches 664 formed therein. The notches 664 are offset from the annular slots 642 and correspond to an annular slot 624 (i.e., desired reaming depth).

Figure 8A:
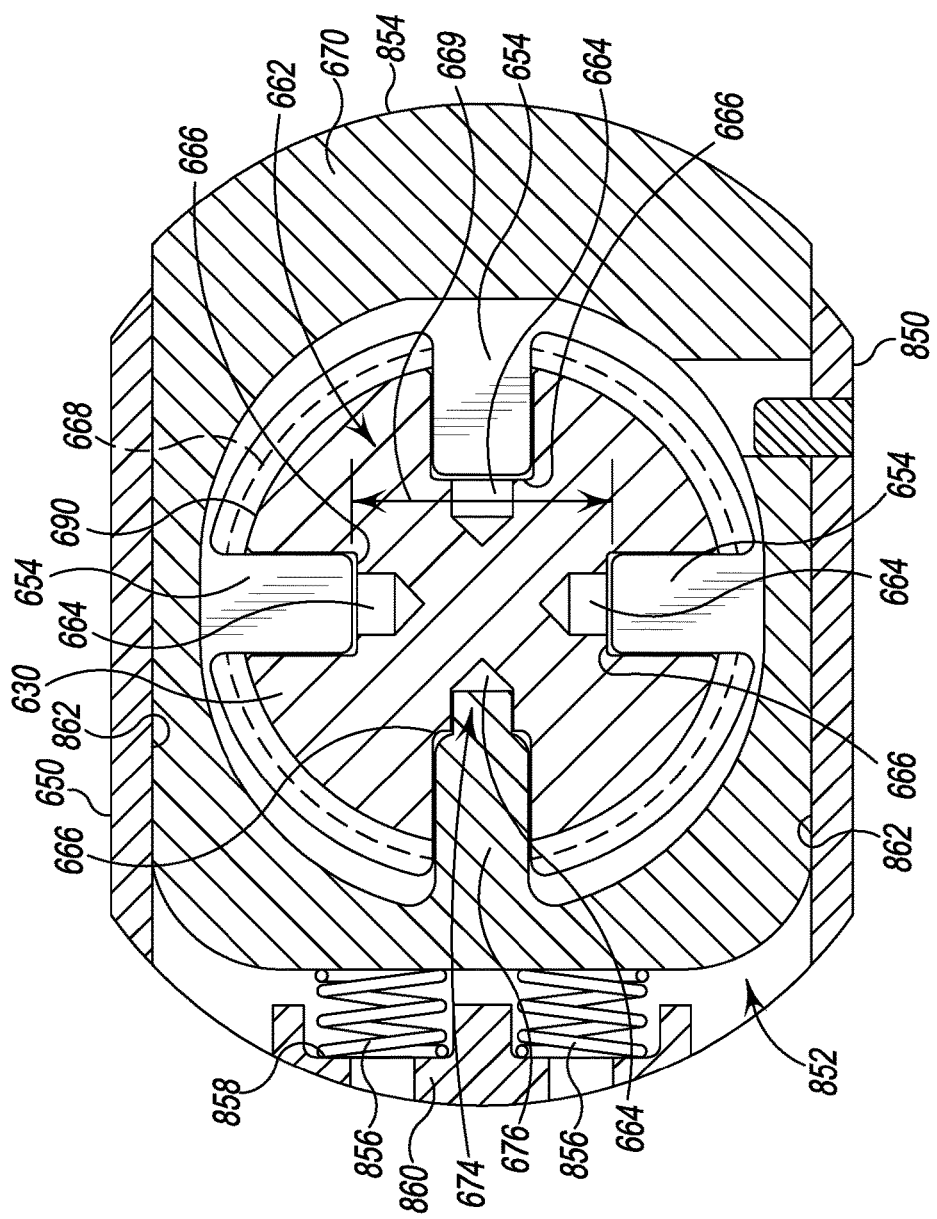
FIG. 8A is a cross-sectional plan view of the instruments of FIG. 8 taken along the line 8-8 in FIG. 8.

As shown in FIG. 8A, the bottom surfaces 666 of the slots 660 of each reamer (illustratively reamer 630 and another reamer 668 having a larger diameter shown in broken line) are positioned and sized to be received in an alignment opening 662 defined by the tips of the tabs 654 so that a single depth stop 650 may be used with any size reamer. In the illustrative embodiment, opposing bottom surfaces 666 define a distance 669 that is the same for every reamer so that a single depth stop 650 may be used with all of the reamers.

In the illustrative embodiment, the depth stop 650 includes a movable plate 670 is connected to a pin 674 that may be advanced into and out of engagement with one of the notches 664 to secure the depth stop at a desired position indicated by the annular slot 642. The pin 674 extends from a flange 676 that is aligned with one of the tabs 654 of the depth stop 650.

As shown in FIG. 8A, the depth stop 650 includes a body 850 defining a cavity 852. The alignment opening 662 extends through the body 850 and through the cavity 852. The moveable plate 670 is positioned within the cavity 852. The moveable plate 670 includes a button 854 extending from an actuating side 856 of the depth stop 650. Springs 856 extend between the moveable plate 670 and a sidewall 858 formed on a retaining side 860 of the depth stop 650 to bias the moveable plate 670 toward an engagement position. A pin in the body 850, which is received in an opening defined in the moveable plate 670, couples the moveable plate 670 to the body 850.

The body 850 of the depth stop 650 includes a pair of planar walls 862 that are configured to engage the guide adapter 620. A plurality of alignment tabs 654 extend from each wall 862. In the illustrative embodiment, the depth stop 650 includes 8 alignment tabs arrange orthogonally to each other. Four opposing alignment tabs 654 (positioned on each side of the plate 670) extend parallel to the pin 674 while the other tabs 654 (also positioned on each side of the plate 670) extend orthogonal to the pin 674.

To secure the depth stop 650 to the reamer 630, the depth stop 650 is advanced along a length of the reamer 630 such that the tabs 654 advance along the longitudinal slots 660. While moving the depth stop 650 along the length of the reamer 630, the button 854 of the depth stop 650 is depressed to move the moveable plate 670 such that the pin 674 is disengaged from the reamer 630.

Figure 9:
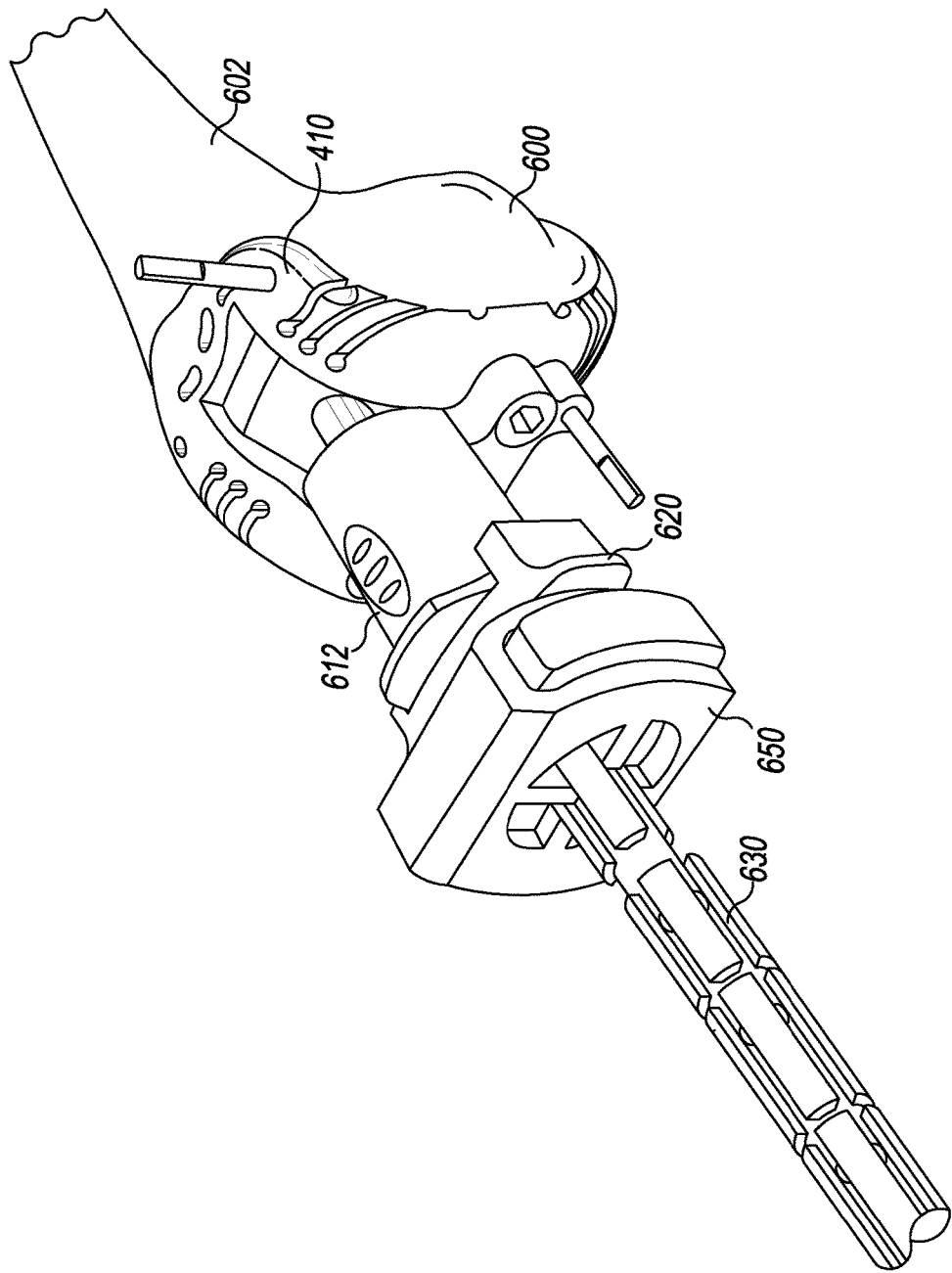

As shown in FIG. 9, when the depth stop 650 is properly positioned at the desired annular slot 642 of the reamer 630, the reamer may be advanced into the central cylindrical passageway 614 of the reaming guide adapter 620 and into contact with the distal end 600 of the patient's femur 602. The surgeon may continue to advance the reamer 630 deeper into the patient's femur until the depth stop 650 contacts the guide adapter 620, thereby forming a surgically-prepared passageway 672 in the distal end 600 of the femur 602, as shown in FIG. 10.

Figure 10:
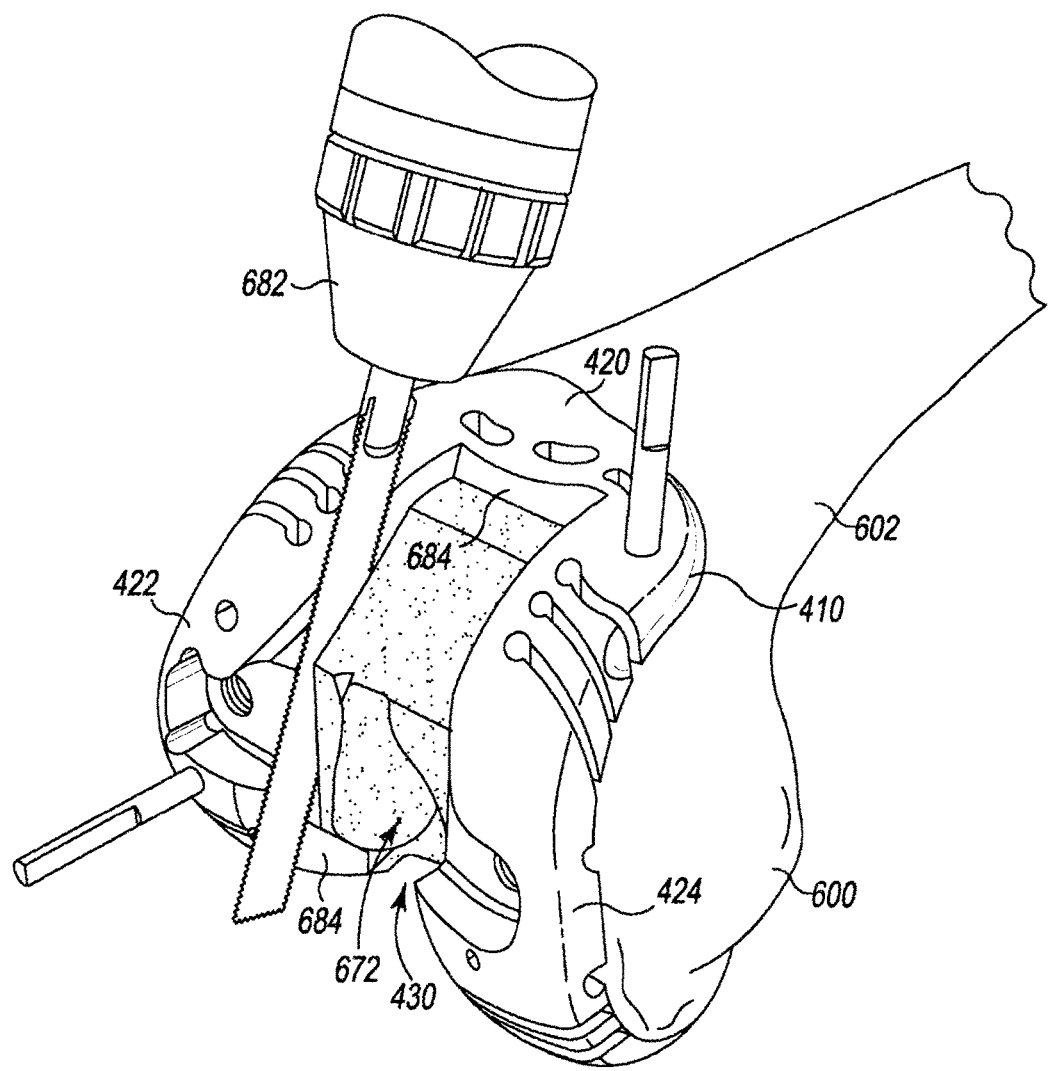

Referring now to FIG. 10, when the surgeon has a passageway 672 of the depth and diameter desired, the reaming guide 610 may be detached from trial component 410. The surgeon may then use a surgical saw 682 perform a "box cut" of the distal end 600 of the patient's femur 602. As described above, the trial component 410 includes a central passageway 430 defined by inner surfaces of the anterior flange 420, the arms 422, 424, and the posterior plate 428 of the component 410. In the illustrative embodiment, the surfaces 684 defining the central passageway 430 are substantially planar surfaces and act as cutting guide surfaces for the surgical saw 682.

Figure 11:
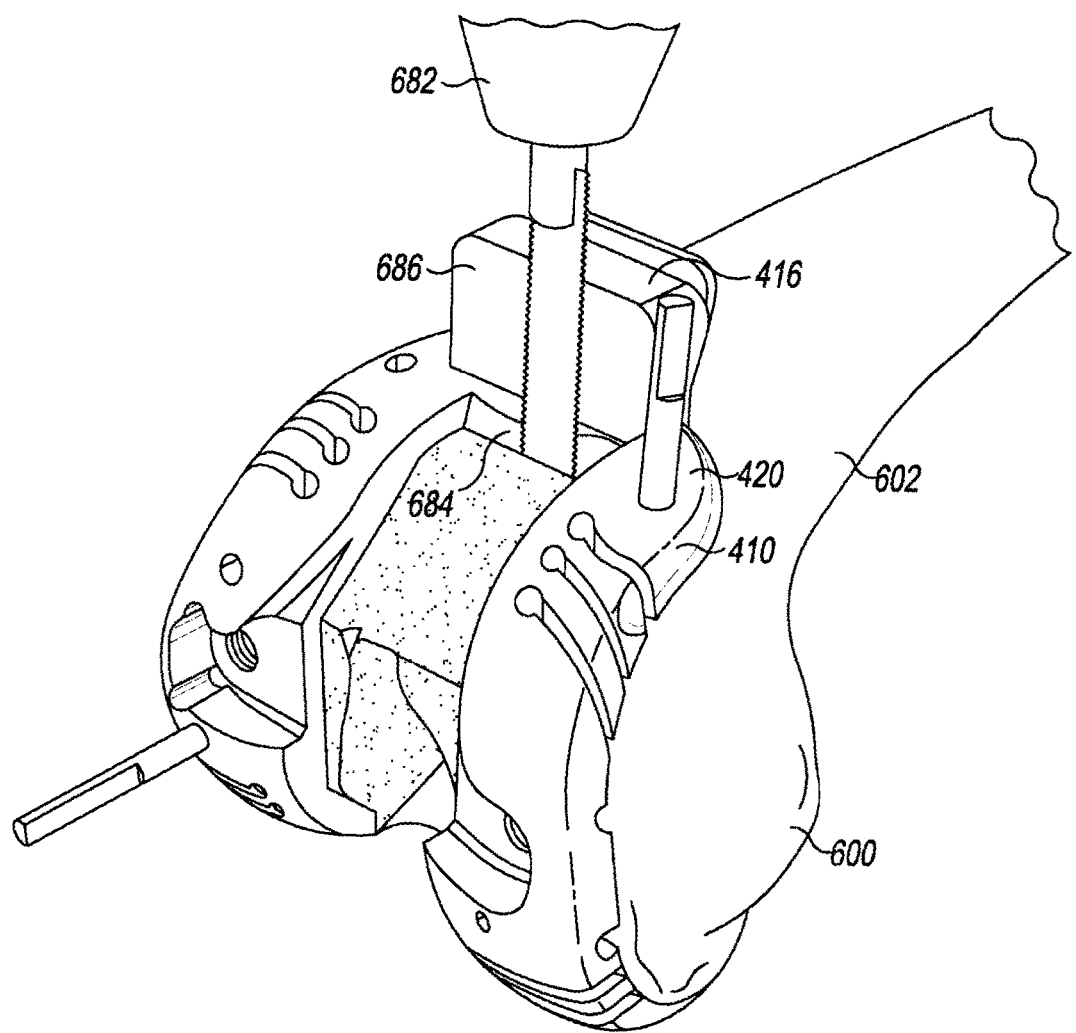
Figure 12:
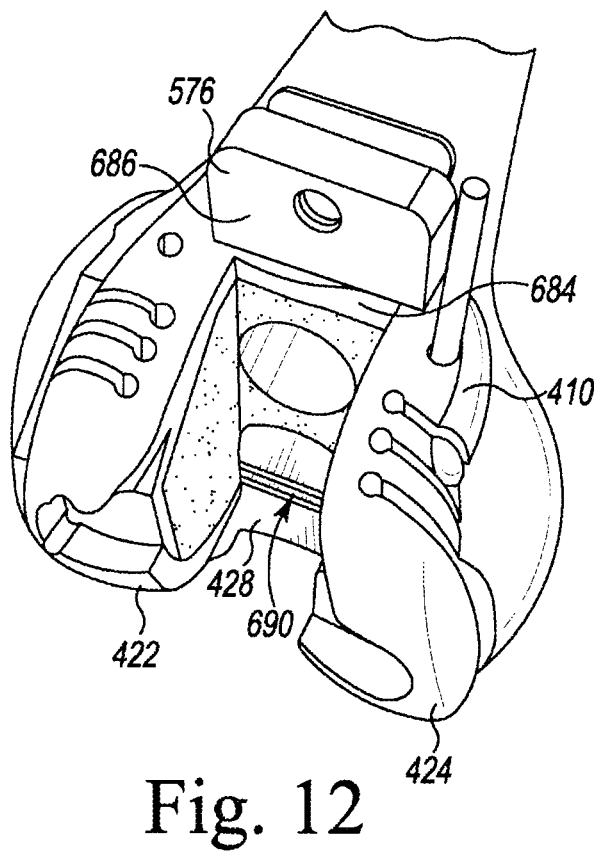
Figure 12A:
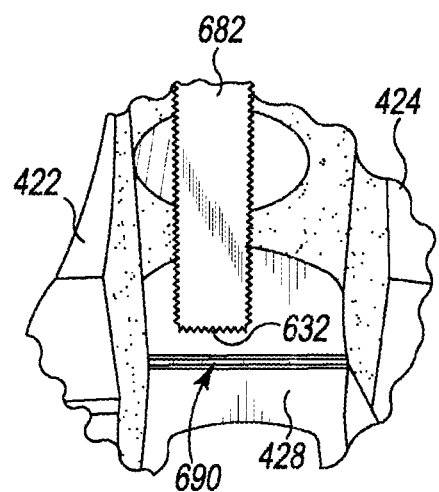

To provide additional support for the distal resection of the box cut, the surgeon may attach the cutting guide platform 416, as shown in FIG. 11. The planar surface 686 of the platform 416 lines with the surface 684 of the anterior flange 420 to provide an extended cutting guide surface for the resection. As shown in FIG. 12, the posterior plate 428 of the trial component 410 includes a groove 690 extending between the arms 422, 424. The groove 690 is sized to receive the cutting edge 692 of the surgical saw 682, thereby acting as a capture for the saw 682. Additionally, the groove 690 provides the surgeon with a visual indication that the desired resection depth has been achieved. When the resection is completed, the surgeon may remove the femoral trial component 410 from the patient's bone.

Referring now to FIGS. 13A and 13B, the surgeon may attach the box trial component 412 to the femoral trial component 410. To do so, the surgeon may align the box trial component 412 with the central passageway 430 of the trial component 410, as shown in FIG. 13A. The surgeon may then advance the body 510 of the box trial component 412 into the central passageway 430 and the mounting flanges 520 into their corresponding apertures 450, 452. As described above, improper alignment of the components 410, 412 is prevented by the combination of notches 530, 532 and tabs 534, 536 formed on the components 410, 412, respectively. With the flanges 520 positioned in the apertures 450, 452, surgeon may advance the fasteners 460 into the threaded holes 456, thereby securing the box trial component 412 to the femoral trial component 410. It should be appreciated that the box trial component 412 may be attached before the femoral trial component 410 is positioned on the bone or after the component 410 is in position.

Figure 14:
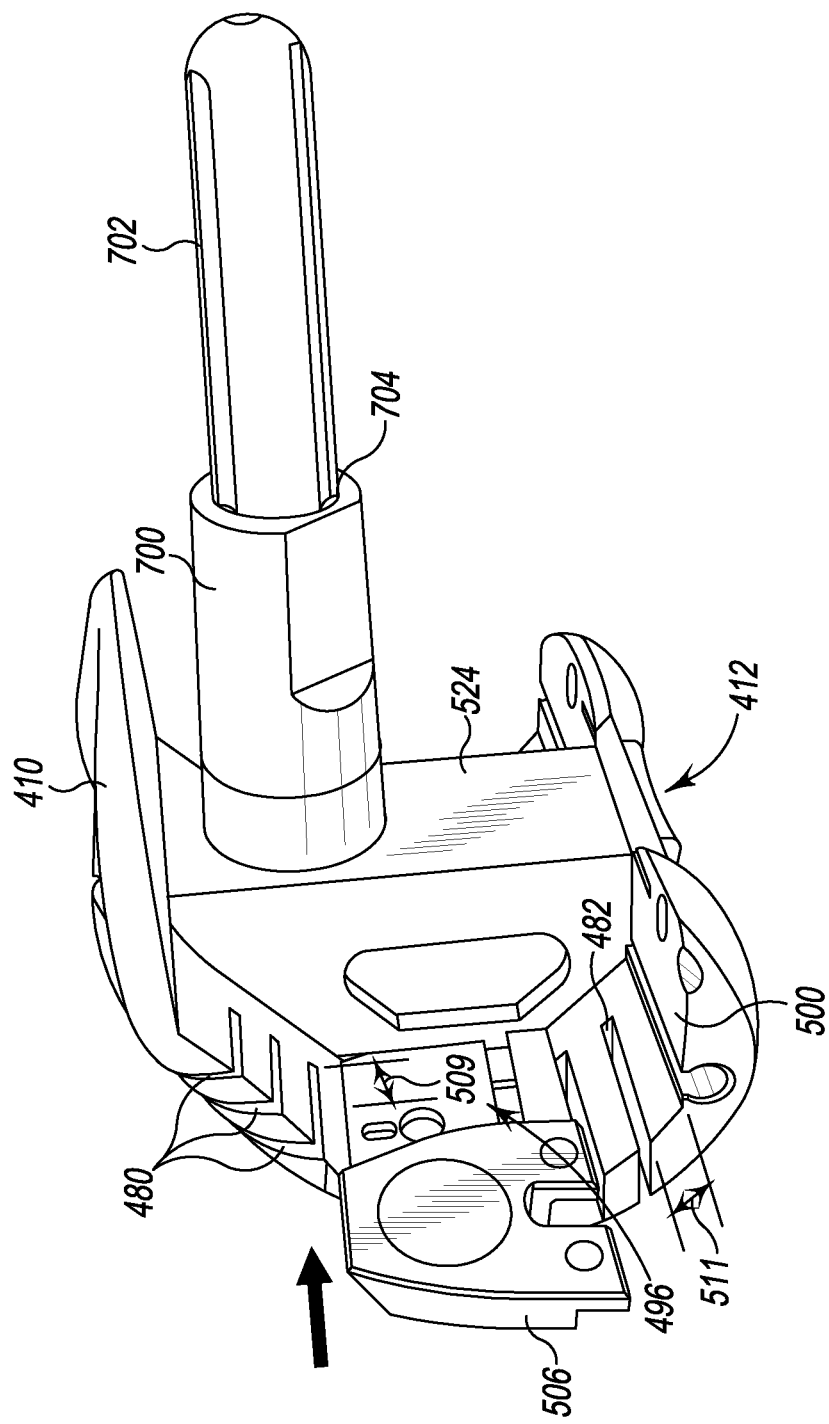

As shown in FIG. 14, the box trial component 412 includes a stem post 700 configured to be secured to a stem trial 702. It should be appreciated that the system 10 may include a number of different stem trials 702 having different lengths and different diameters, sized to fit bones of varying sizes. To secure the stem trial 702 to the post 700, one end of the stem trial 702 is aligned with an opening 704 defined in the stem post 700 and then advanced into the opening 704. As shown in FIGS. 13A and 13B, a threaded fastener 706 is advanced between the arms 514, 516 of the box trial component 412 and into the passageway of the stem post 700. The fastener 706 is threaded into an opening (not shown) defined in the end of the stem trial 702 to secure the stem trial 702 to the trial component 412.

Turning again to FIG. 14, the surgeon may optionally attach one or more femoral augment trials 506 to the femoral trial component 410. To do so, surgeon may align a tab (not shown) of the trial 506 with one of the mounting slots 502 defined in the trial component 410. The surgeon may then advance the trial 506 into the mounting slot 502, thereby securing the trial components together. The surgeon may introduce the assembly into the surgically prepared distal end 600 of the patient's femur 602 and perform a trial reduction to evaluate the range of motion with the femoral trial component 410 attached to the bone. Alternatively, the trials 506 may be inserted into the slots 502 with the femoral trial component 410 already positioned on the bone.

Figure 20:
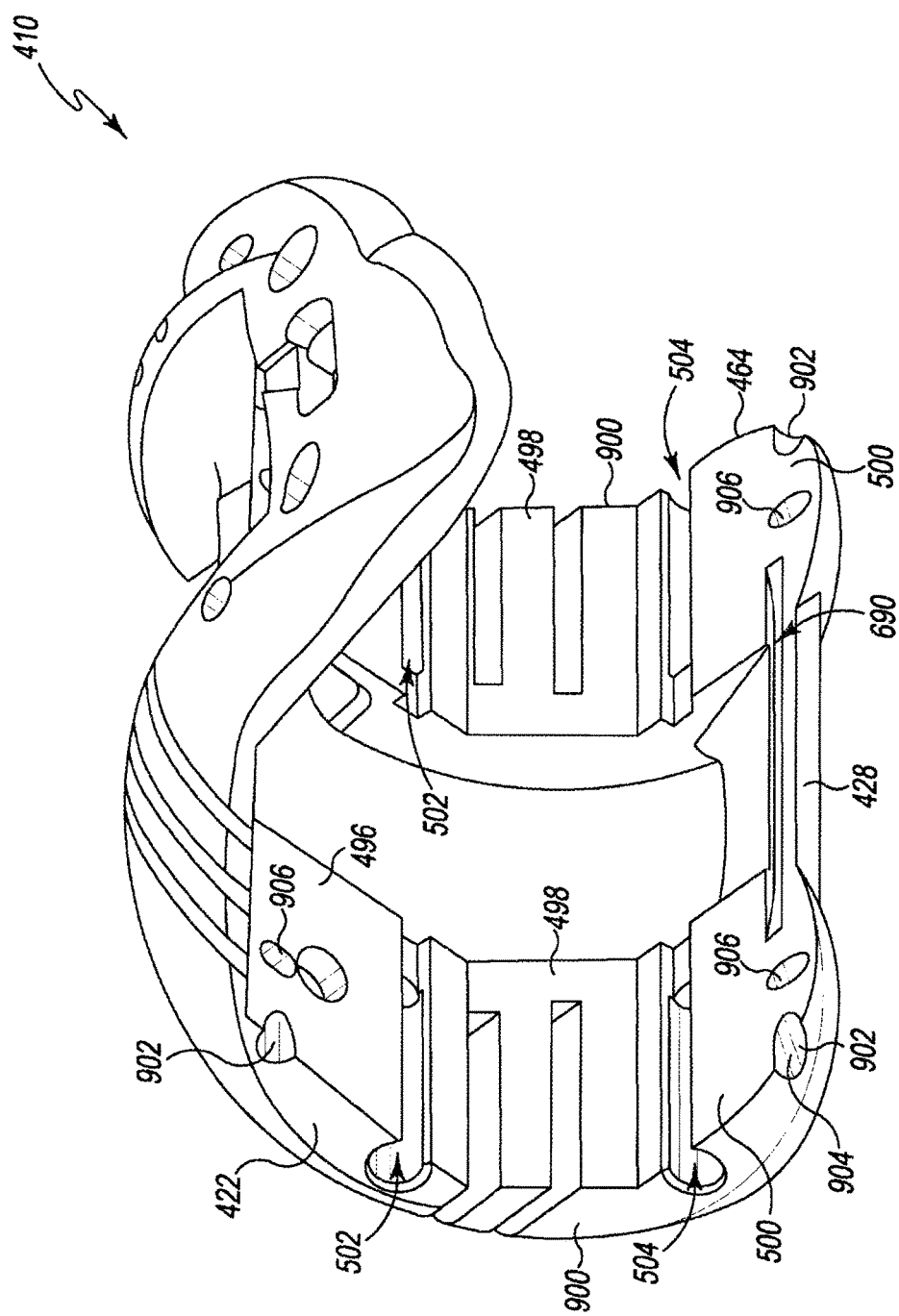
FIG. 20 is a proximal perspective view of the femoral cutting guide of FIGS. 9-5.

Referring to FIG. 20, each curved arm 422, 424 includes the mounting slot 502 defined in its distal bone-facing surface 496. The mounting slot 502 extends inwardly from an outer edge 900 of the arm 422, 424. It should be appreciated that the outer edge may be the medial or lateral edge of the femoral trial component. A channel 902 is defined in the distal bone-facing surface 496 of each arm 422, 424 and extends inwardly from the outer edge 900 parallel to the slot 502. The channel 902 is partially defined by a tapered surface 904. An aperture 906 is defined in the distal bone-facing surface 496 of each arm 422, 424 and is spaced apart from the channel 902.

Additionally, each curved arm 422, 424 includes the mounting slot 502 defined in its posterior bone-facing surface 500. The mounting slot 502 extends inwardly from an outer edge 900 of the arm 422, 424. A channel 902 is defined in the posterior bone-facing surface 500 of each arm 422, 424 and extends inwardly from the outer edge 900 parallel to the slot 502. The channel 902 is partially defined by a tapered surface 904. An aperture 906 is defined in the posterior bone-facing surface 500 of each arm 422, 424 and is spaced apart from the channel 902.

Referring to FIGS. 21 and 22, a plurality of augment trial components 506 are sized to be positioned on one of the distal bone-facing surface 496 or the posterior bone-facing surface 500 of the arms 422, 424. Particularly, the augment trial components 506 include distal augment trial components and posterior augment trial components. The augment trial components 506 include at least one magnet and may be made from a magnetic material.

Each augment trial component 506 has a different thickness 507 defined between a planar base surface 903 and a planar bottom surface 907. In a distal augment trial component 506, the thickness 507 is equal to a spacing 509 (shown in FIG. 14) defined between the bone-facing surfaces 496 and the distal cutting slots 480 of each arm 422, 424. In a posterior augment trial component 506, the thickness 507 is equal to a spacing 511 (shown in FIG. 14) defined between the bone-facing surfaces 500 and the posterior cutting slots 482 of each arm 422, 424. The planar base surface 903 is configured to engage one of the bone-facing surfaces 496, 500 of the curved arms 422, 424. In a distal augment trial component 506, a flange 913 extends from a front 915 of the component 506. It should be noted that a posterior augment trial component 506 does not include the flange 913. The trials 506 include mounting posts 908 and a peg 910 extending outwardly from the planar base surface 903. The mounting posts 908 have substantially cylindrical ends 915.

The slots 502 formed in the arm 422, 424 are sized to receive the mounting posts 908 of one of the plurality of trials 506. Particularly, the slots are sized and shaped to receive the cylindrical ends 915 of the mounting posts 908. The mounting posts 908 include a pin 914 that is operable to retain the cylindrical ends 915 of the mounting posts 908 in the slot 502 of the curved arm 422, 424. The peg 910 is sized to be received in the channel 902. Particularly, the tapered surface 904 of the channel 902 is configured to engage the peg 910 of each trial 506 as the trial 506 is advanced into the arm 422, 424. The aperture 906 is sized to receive the peg 910 of each trial 506 when the trial 506 is fully advanced into the slot 502.

Figure 23:
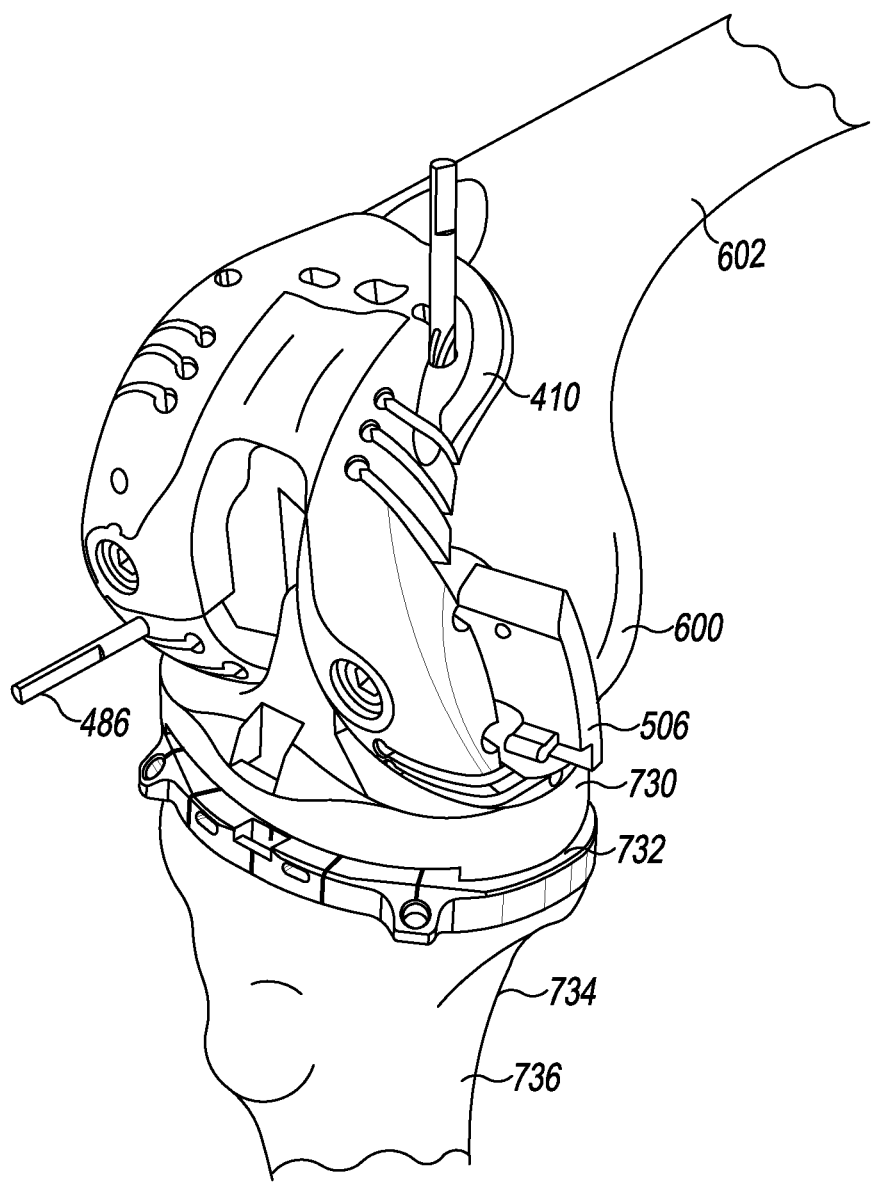
FIG. 23 is a further illustration of a step of the orthopaedic surgical procedure using the orthopaedic joint replacement system.

As illustrated in FIG. 23, after positioning the femoral trial component 410 on the patient's femur, the surgeon may advance the trial 506 into one of the mounting slot 502 of the component 410. As the trial 506 is advanced medially or laterally from the outer edge into the mounting slot 502, the peg 910 engages the tapered surface 904, thereby causing the trial 506 to tilt relative to the bone-facing surface of the femoral trial component. The peg 910 may exit the channel 902, slide along the bone-facing surface, and then drop into the aperture 906. In this position, the peg 910 of the trial 506 is retained in the aperture 906 component 410 to retain the trial 506 and prevent the trial 506 from retracting through the mounting slot 502. Additionally, the trial 506 magnetically couples to the component 410 to further retain the trial 506.

Returning to FIGS. 15A-B, the femoral trial component 410 may be utilized with other trial components including, for example, a post trial component 712. Similar to the box trial component 412, the post trial component 712 includes an anterior flange 512 and a pair of arms 514 extending from the flange 512. A pair of mounting flanges 520 extend outwardly from the arms 514 and are configured to be received in the apertures 450, 452 of the femoral trial component 410. A stem post 700 extends away from the arms 514 of the post trial component 712.

The system 10 also includes a boss trial 714 configured to be secured to the stem post 700 via the threaded fastener 706. As shown in FIG. 16, the boss trial 714 has a threaded bore 716 sized to receive a corresponding threaded shaft 718 of a stem trial component 720. A driver tool 722 may be used to thread the stem trial component 720 onto the boss trial 714.

Figure 17:
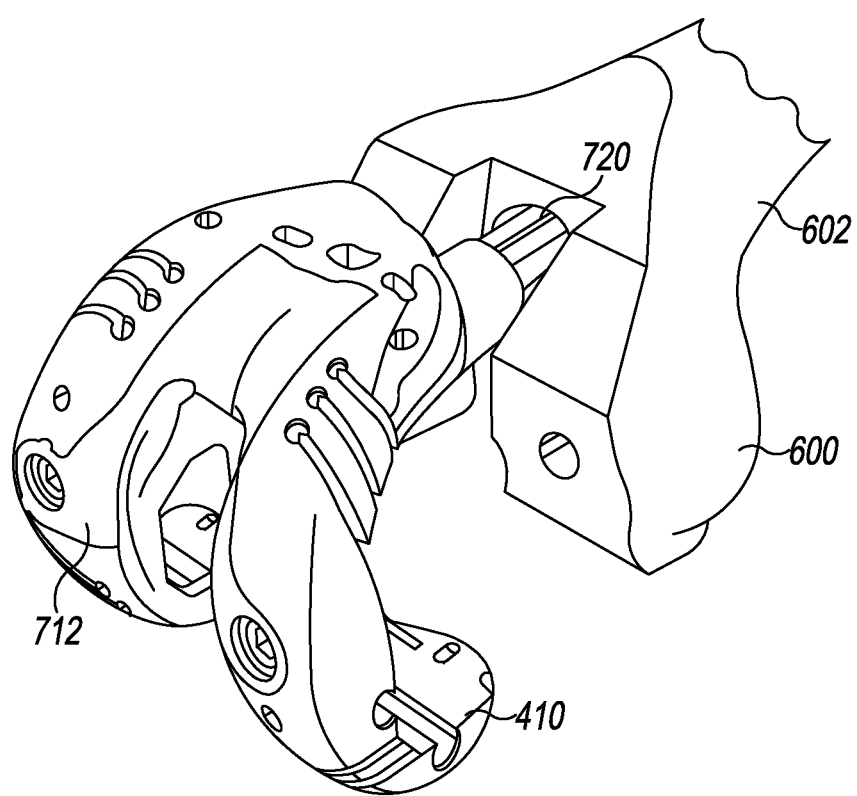
Figure 18:
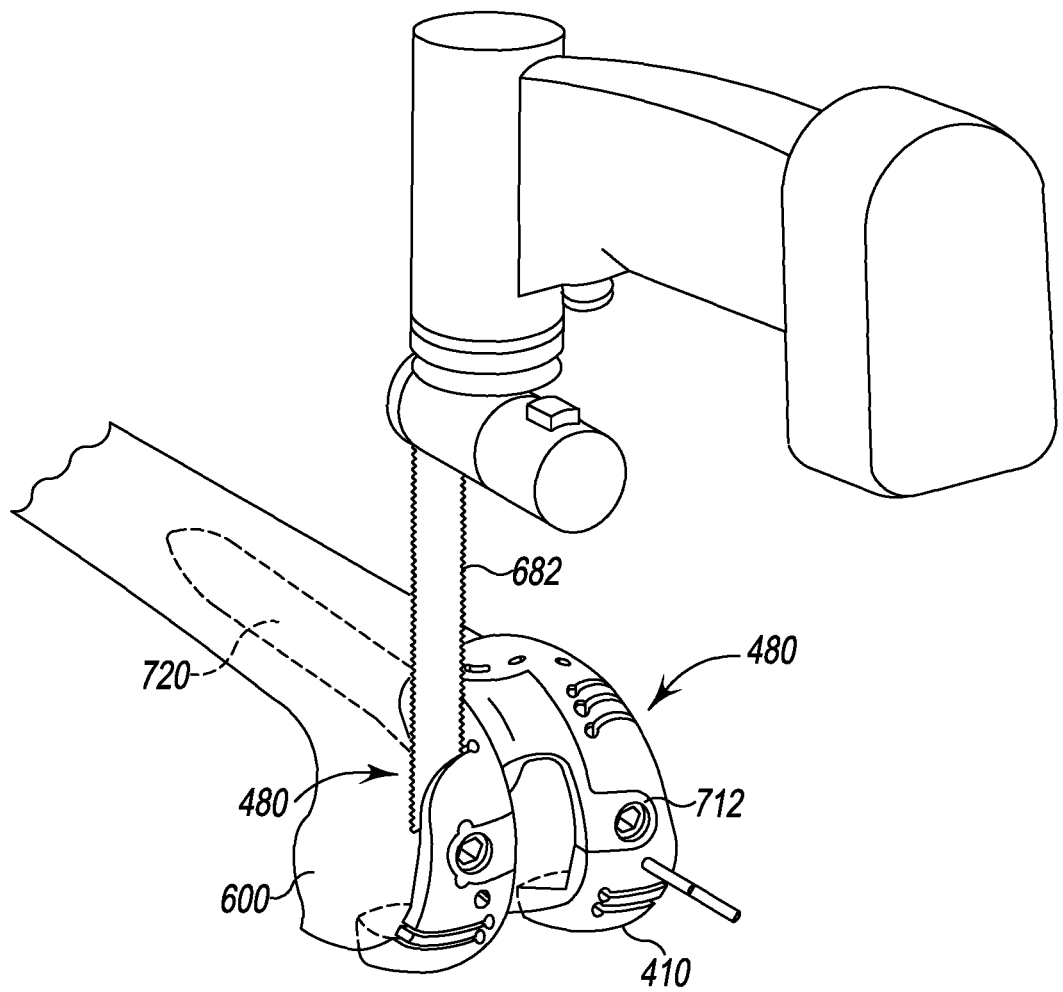

Referring now to FIG. 17 the assembled trial component 410, post trial component 712, and stem trial component 720 may be advanced onto the distal end 600 of the patient's femur 602. It should be appreciated that the post trial component 712, like the other femoral trial insert components, may be attached before the femoral trial component 410 is positioned on the bone or after the component 410 is in position. As shown in FIG. 18, with the assembly positioned on the distal end 600, a surgeon may use a surgical saw 682 to resect the patient's bone. To do so, the surgeon may position the saw 682 in the one of the cutting guide slots 480 to remove a desired amount of bone from the distal end 600. As shown in FIG. 17, the surgeon may utilize the cutting guide slot 480 to remove sufficient bone material to permit the insertion of an augment trial 506, as described above. The surgeon may continue the resection to shape the bone as desired to receive a femoral prosthetic component 20.

Figure 19:
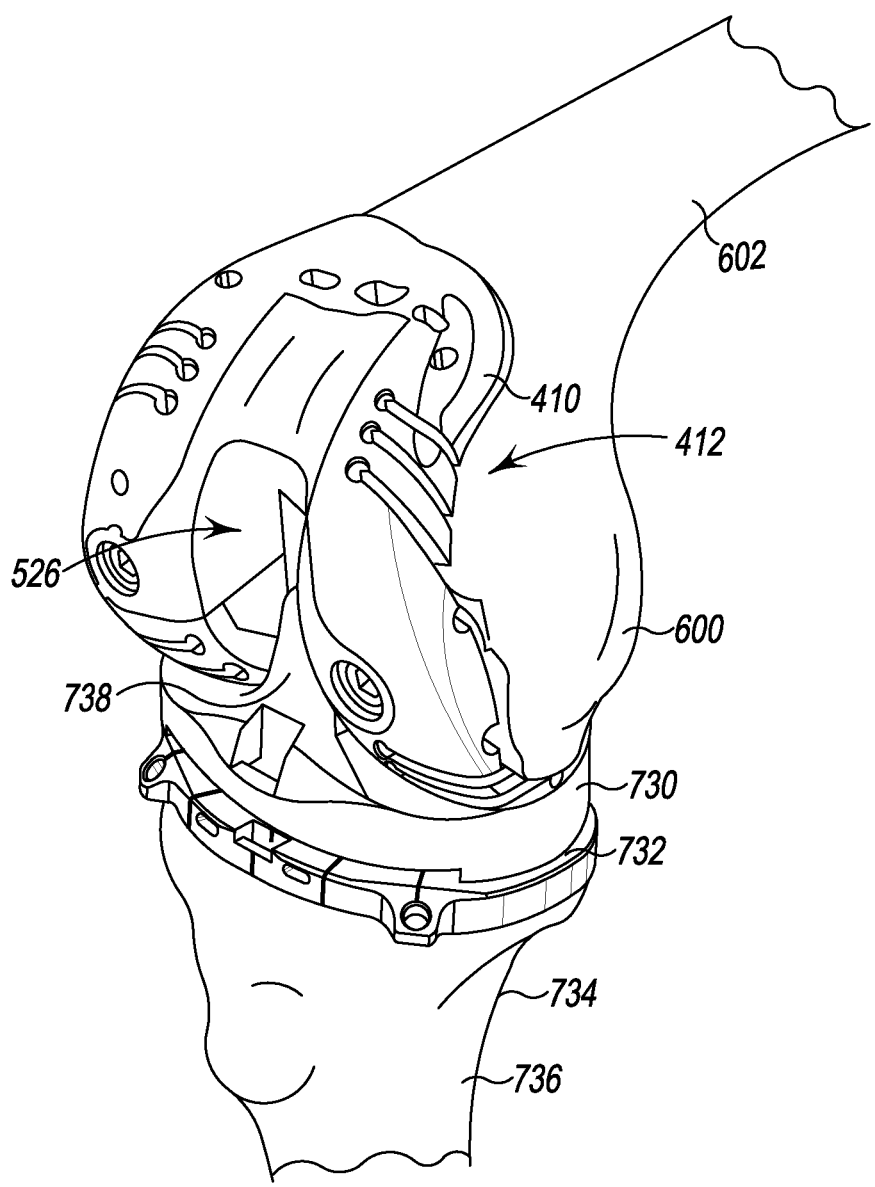

As described above, the femoral trial component 410 and the box trial component 412 and/or the post trial component 712 may be used during a trial reduction to evaluate the range of motion. As shown in FIG. 19, the femoral trial component 410 is configured to engage a tibial insert trial component 730 positioned on a tibial base trial component 732, which is attached to the proximal end 734 of a patient's tibia 736. An exemplary description of trial reduction and preparation of patient's tibia is disclosed in U.S. Pat. No. 9,028,501, issued on May 12, 2015 and entitled "TIBIAL ORTHOPAEDIC SURGICAL INSTRUMENTS AND METHOD OF USING SAME" by Kyle B. Thomas et al., which is incorporated herein by reference. The tibial insert trial component includes a pair of concave curved surfaces that engage and articulate with the surfaces of the femoral trial component 410 and the box trial component 412 and/or the post trial component 712 over a range of flexion from extension to flexion to evaluate the range of motion and determine the appropriately-sized prosthesis.

It should be appreciated that the surgeon may perform an initial trial reduction with the post trial component 712 and stem trial component 720. The surgeon may then remove the post trial component 712 and stem trial component 720 while leaving the femoral trial component 410 in position on the patient's femur. The surgeon may then perform the reaming operation described above in regard to FIGS. 7 and 9, perform the box cut operation described above in regard to FIGS. 10-12, and then attach the box trial component 412 before performing an additional trial reduction and/or augment resection as described.

While the foregoing exemplary embodiments have been described to have a separable tibial tray and a tibial tray insert, it is to be understood that the tibial tray may include condyle receiver bearing surfaces that obviate the need for a separate tibial tray insert.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

The invention claimed is:

1. An orthopaedic surgical system comprising:
a femoral trial component configured to be coupled to a surgically-prepared distal end of a patient's femur, the femoral trial component comprising an anterior flange, a pair of curved arms extending away from the anterior flange, a posterior flange extending between the pair of curved arms, and a central passageway defined between the anterior flange, the curved arms, and the posterior flange, each arm including a curved condyle surface, a distal bone-facing surface, a plurality of anterior cutting guide slots, and a plurality of distal cutting guide slots,
a femoral trial insert component configured to be secured to the femoral trial component, the femoral trial insert component including a main body sized to be positioned in the central passageway of the femoral trial component between the pair of curved arms,
a plurality of augment trial components, each augment trial component being sized to be positioned on the distal bone-facing surface, and
a cutting block that is configured to be releasably coupled to an anterior surface of the anterior flange of the femoral trial component, the cutting block comprising a cutting guide surface,
wherein when the cutting block is coupled to the anterior flange of the femoral trial component, the cutting guide surface is positioned coplanar with a distal surface of the anterior flange of the femoral trial component and the posterior flange of the femoral trial component is aligned with the cutting guide surface of the cutting block to prevent further posterior movement of a cutting saw blade,
wherein the main body of the femoral trial insert component includes (i) an anterior flange having a curved surface that is shaped to match a patella surface of a prosthetic femoral component, (ii) a pair of arms spaced apart from one another and extending parallel to one another away from the anterior flange of the main body, and (iii) a pair of mounting flanges each extending outwardly from each of the pair of arms in opposite directions,
wherein each of the curved arms of the femoral trial component includes an aperture defined in the curved arm that opens into the central passageway of the femoral trial component, each aperture being sized and shaped to receive one of the pair of mounting flanges of the femoral trial insert component to secure the femoral trial component to the femoral trial insert component, wherein the cutting block includes a locking mechanism operable to secure the cutting block to the femoral trial component, wherein:

the anterior flange of the femoral trial component includes a slot, and the locking mechanism including (i) a moveable locking tab extending outwardly from a body of the cutting block that is sized to be received in the slot, the locking tab being moveable between a first position in which the locking tab is configured to engage the anterior flange of the femoral trial component to secure the cutting block to the femoral trial component and a second position in which the locking tab is configured to be spaced apart from the anterior flange of the femoral trial component, and (ii) a biasing element to bias the locking tab in the first position.

2. The orthopaedic surgical system of claim 1, wherein:

each aperture of the femoral trial component and each mounting flange of the pair of mounting flanges of the femoral trial insert component includes a through-hole configured to receive a fastener, the fastener being configured to secure the femoral trial component to the femoral trial insert component when the pair of mounting flanges are positioned in the apertures.

* * * * *